US012023018B2

(12) United States Patent
Harari

(10) Patent No.: US 12,023,018 B2
(45) Date of Patent: Jul. 2, 2024

(54) ANCHORING DEVICE AND METHOD FOR ACCURATE POSITIONING AND INSERTION OF AN ANCHOR ASSEMBLY

(71) Applicant: FEMSELECT LTD., Modi'in (IL)

(72) Inventor: Boaz Harari, Ganei-Tikva (IL)

(73) Assignee: FEMSELECT LTD., Mod'in (IL)

( * ) Notice: Subject to any disclaimer, the term of this patent is extended or adjusted under 35 U.S.C. 154(b) by 775 days.

(21) Appl. No.: 16/468,379

(22) PCT Filed: Dec. 15, 2016

(86) PCT No.: PCT/IL2016/051338
§ 371 (c)(1),
(2) Date: Jun. 11, 2019

(87) PCT Pub. No.: WO2018/109755
PCT Pub. Date: Jun. 21, 2018

(65) Prior Publication Data
US 2021/0128136 A1    May 6, 2021

(51) Int. Cl.
*A61B 17/04* (2006.01)
*A61B 17/00* (2006.01)
(Continued)

(52) U.S. Cl.
CPC .......... *A61B 17/0401* (2013.01); *A61B 42/20* (2016.02); *A61B 2017/00438* (2013.01);
(Continued)

(58) Field of Classification Search
CPC ................ A61B 17/0401; A61B 42/20; A61B 2017/00438; A61B 2017/0409; A61B 2017/3405
See application file for complete search history.

(56) References Cited

U.S. PATENT DOCUMENTS 4,877,033 A   10/1989   Seitz, Jr.
5,220,690 A    6/1993   Hoos
(Continued)

FOREIGN PATENT DOCUMENTS

CA   2093824   10/1994
DE   2910410   12/1979
(Continued)

OTHER PUBLICATIONS

An International Search Report and a Written Opinion both dated Mar. 17, 2017, which issued during the prosecution of Applicant's PCT/IL2016/051338.
(Continued)

*Primary Examiner* — Tan-Uyen T Ho
*Assistant Examiner* — David P Stein
(74) *Attorney, Agent, or Firm* — McDonnell Boehnen Hulbert & Berghoff LLP

(57) ABSTRACT

An anchoring device including a finger-mountable work channel defining assembly defining a finger mounting axis and a work channel axis angled with respect to the finger mounting axis, the finger-mountable work channel defining assembly defining an aperture lying generally in an aperture plane angled with respect to the finger mounting axis and with respect to the work channel axis, an anchor insertion assembly arranged for limited axial displacement along the work channel axis with respect to the aperture so as to intersect the aperture plane and an anchor assembly including at least an anchoring portion and a flexible elongate portion attached thereto, the anchoring portion having a pre-anchoring operative orientation and an anchoring operative orientation.

20 Claims, 39 Drawing Sheets

(51) Int. Cl.
*A61B 17/34* (2006.01)
*A61B 42/20* (2016.01)
(52) U.S. Cl.
CPC ............... *A61B 2017/0409* (2013.01); *A61B 2017/3405* (2013.01)

(56) References Cited

U.S. PATENT DOCUMENTS

| | | | |
|---|---|---|---|
| 5,441,050 | A | 8/1995 | Thurston |
| 5,693,041 | A | 12/1997 | Murphy-Chutorian |
| 5,829,880 | A | 11/1998 | Diedrich |
| 6,066,104 | A | 5/2000 | Dao et al. |
| 6,332,888 | B1 | 12/2001 | Levy et al. |
| 6,355,017 | B2 | 3/2002 | Buttgen et al. |
| 6,506,190 | B1 | 1/2003 | Walshe |
| 6,602,251 | B2 | 8/2003 | Burbank et al. |
| 7,393,319 | B2 | 7/2008 | Merade et al. |
| 8,257,366 | B2 | 9/2012 | Schneider et al. |
| 8,535,216 | B2 | 9/2013 | Chu et al. |
| 8,617,183 | B2 | 12/2013 | Schneider et al. |
| 9,451,944 | B2 | 9/2016 | Schneider et al. |
| 9,517,058 | B2 | 12/2016 | Harari et al. |
| 9,737,391 | B2 | 8/2017 | Harari et al. |
| 10,098,664 | B2 | 10/2018 | Harari et al. |
| 10,390,924 | B2 | 8/2019 | Harari |
| 2001/0041914 | A1* | 11/2001 | Frazier ............... A61B 17/0057 606/225 |
| 2002/0077631 | A1 | 6/2002 | Lubbers et al. |
| 2004/0002735 | A1* | 1/2004 | Lizardi ................. A61F 2/0811 606/232 |
| 2004/0244511 | A1 | 12/2004 | Hueftle et al. |
| 2005/0234305 | A1 | 10/2005 | Licciardi |
| 2005/0250987 | A1 | 11/2005 | Ewers et al. |
| 2006/0047285 | A1 | 3/2006 | Fields |
| 2007/0142846 | A1* | 6/2007 | Catanese, III ........ A61F 2/0063 606/142 |
| 2007/0239208 | A1 | 10/2007 | Crawford |
| 2008/0064962 | A1 | 3/2008 | Oonuki et al. |
| 2008/0171940 | A1 | 7/2008 | McGahan |
| 2008/0207988 | A1 | 8/2008 | Hanes |
| 2008/0208216 | A1 | 8/2008 | Cerier |
| 2009/0012557 | A1 | 1/2009 | Osypka |
| 2009/0216075 | A1 | 8/2009 | Bell et al. |
| 2010/0274074 | A1 | 10/2010 | Khamis et al. |
| 2011/0092985 | A1 | 4/2011 | Gaynor et al. |
| 2011/0092986 | A1 | 4/2011 | Gaynor et al. |
| 2011/0092991 | A1 | 4/2011 | Gaynor et al. |
| 2011/0196389 | A1 | 8/2011 | Schneider et al. |
| 2012/0123410 | A1 | 5/2012 | Craig |
| 2014/0100580 | A1 | 4/2014 | Yu et al. |
| 2014/0324072 | A1 | 10/2014 | Harari et al. |
| 2015/0005586 | A1 | 1/2015 | Williams |
| 2015/0320442 | A1 | 11/2015 | Harari et al. |
| 2016/0235461 | A1 | 8/2016 | Sumko |
| 2017/0049548 | A1 | 2/2017 | Harari et al. |
| 2017/0196671 | A1 | 7/2017 | Harari et al. |
| 2017/0348085 | A1 | 12/2017 | Harari |
| 2019/0008558 | A1 | 1/2019 | Harari et al. |
| 2019/0290420 | A1* | 9/2019 | Dougherty ............ A61F 2/0805 |

FOREIGN PATENT DOCUMENTS

| | | |
|---|---|---|
| DE | 10321012 | 12/2004 |
| DE | 20 2014 103 998 U1 | 9/2014 |
| EP | 1862134 | 5/2007 |
| EP | 3 113 291 A1 | 1/2017 |
| JP | 2004-509685 | 4/2004 |
| JP | 2008-510589 | 4/2008 |
| JP | 2008-523926 | 7/2008 |
| JP | 2017518114 | 7/2017 |
| KR | 101115493 | 3/2012 |
| WO | 95/14438 | 6/1995 |
| WO | 2011/047685 | 4/2011 |
| WO | 2011/082350 | 7/2011 |
| WO | 2012/047626 | 4/2012 |
| WO | 2013/093924 | 6/2013 |
| WO | 2015/189843 | 12/2015 |
| WO | 2015189843 | 12/2015 |
| WO | 2018/109755 | 6/2018 |

OTHER PUBLICATIONS

An International Search Report and a Written Opinion both dated Nov. 2, 2015, which issued during the prosecution of Applicant's PCT/IL2015/050585.
An International Preliminary Report on Patentability dated Dec. 15, 2016, which issued during the prosecution of Applicant's PCT/IL2015/050585.
An International Search Report and a Written Opinion both dated May 9, 2013. which issued during the prosecution of Applicant's PCT/IL2012/050548.
An International Preliminary Report on Patentability dated Oct. 21, 2014, which issued during the prosecution of Applicant's PCT/IL2012/050548.
Rofaeel, A., M.D., Peng, Philip, M.B.B.S., F.R.C.P.C., Louis, I., M.D., & Chan, Vincent, M.D., F.R.C.P.C. (2008). Feasibility of real-time ultrasound for pudendal nerve block in patients with chronic perineal pain. Regional Anesthesia and Pain Medicine, 33(2), 139-45.
An Office Action dated Apr. 8, 2016, which issued during the prosecution of U.S. Appl. No. 14/366,002.
An International Preliminary Report on Patentability dated Jun. 18, 2017, which issued during the prosecution of Applicant's PCT/IL2016/051338.
An Office Action dated Nov. 5, 2015, which issued during the prosecution of U.S. Appl. No. 14/366,002.
Notice of Allowance dated Aug. 12. 2016, which issued during the prosecution of U.S. Appl. No. 14/366,002.
Notice of Allowance dated May 12. 2017, which issued during the prosecution of U.S. Appl. No. 15/342,144.
An Office Action dated Jan. 17, 2017, which issued during the prosecution of U.S. Appl. No. 15/342,144.
U.S. Appl. No. 61/989,623, filed May 7, 2014.
Notice of Allowance dated Jun. 19, 2018, which issued during the prosecution of U.S. Appl. No. 14/667,954.
Notice of Allowance dated Jul. 10. 2018, which issued during the prosecution of U.S. Appl. No. 14/667,954.
U.S. Appl. No. 62/009,946, filed Jun. 10, 2014.
An English translation of an Office Action dated Oct. 10, 2017 which issued during the prosecution of Japanese Patent Application No. 2016-572283.
An Office Action dated Nov. 15. 2017, which issued during the prosecution of U.S. Appl. No. 14/667,954.
U.S. Appl. No. 61/578,261, filed Dec. 21, 2011.
An English translation of an Office Action dated Dec. 19, 2017, which issued during the prosecution of Japanese Patent Application No. 2016-572283.
An Office Action dated Jun. 22. 2017, which issued during the prosecution of U.S. Appl. No. 14/667,954.
An Advisory Action dated Feb. 28, 2018, which issued during the prosecution of U.S. Appl. No. 14/667,954.
An Office Action dated Oct. 4, 2018, which issued during the prosecution of U.S. Appl. No. 15/651,472.
An English translation of an Office Action dated Aug. 23. 2018, which issued during the prosecution of Chinese Patent Application No. 201580031142.7.
An Office Action dated Jul. 10. 2017, which issued during the prosecution of Singapore Patent Application No. 11201610287V.
An Office Action dated Jan. 23, 2019, which issued during the prosecution of U.S. Appl. No. 15/651,472.
European Search Report dated Dec. 21, 2017 which issued during the prosecution of Applicant's European App No. 15806208.3.
An Office Action dated Aug. 1, 2019, which issued during the prosecution of Australian Patent Application No. 2015273060.
An Office Action dated Apr. 1, 2019, which issued during the prosecution of Australian Patent Application No. 2015273060.

(56) References Cited

OTHER PUBLICATIONS

Notice of Allowance dated May 2, 2019, which issued during the prosecution of U.S. Appl. No. 15/651,472.
An Office Action dated Apr. 29, 2019, which issued during the prosecution of Chinese Patent Application No. 201580031142.7.
The International Search Report (ISR) for PCT/IL2019/050192, dated May 23, 2019, pp. 1-5.
Written Opinion of the International Searching Authority for PCT/IL2019/050192, dated May 23, 2019, pp. 1-5.
Singapore Written Opinion dated Mar. 8, 2021 based on Singapore Patent Application No. 11201905042S.
Office Action dated Dec. 22, 2020 issued against U.S. Appl. No. 15/316,698.
Non-Final Office Action from U.S. Appl. No. 15/316,698; dated Jan. 7, 2020, pp. 1-15.
Notice of Allowance dated Apr. 8, 2021, which issued during the prosecution of U.S. Appl. No. 15/316,698.
An Office Action dated Aug. 13, 2021, which issued during the prosecution of Indian Patent Application No. 201947028179.
An Office Action dated Dec. 23, 2021, which issued during the prosecution of Canadian Patent Application No. 2,951,506.
An Office Action together with an English summary dated Jan. 27, 2022, which issued during the prosecution of Korean Patent Application No. 10-2017-7000766.
An English summary of an Office Action dated Feb. 16, 2022 which issued during the prosecution of Chinese Patent Application No. 201680092073.5.

* cited by examiner

ANCHORING DEVICE AND METHOD FOR ACCURATE POSITIONING AND INSERTION OF AN ANCHOR ASSEMBLY

CROSS-REFERENCE TO RELATED APPLICATION

This application is a U.S. national phase of International Application No. PCT/IL2016/051338, filed on Dec. 15, 2016, which is incorporated by reference herein in its entirety.

REFERENCE TO RELATED APPLICATIONS

Reference is hereby made to PCT Patent Application No. PCT/IL2015/050585, filed Jun. 10, 2015, and entitled TISSUE REPAIR DEVICE AND METHOD, published as Published PCT Patent Application No. WO 2015/189843, to U.S. Published Patent Application No. 2015/0320442, filed Mar. 25, 2015 and entitled SYSTEM AND METHOD FOR PELVIC FLOOR PROCEDURES, and to U.S. Published Patent Application No. 2014/0324072, filed Jun. 17, 2014 and entitled SYSTEM AND METHOD FOR PELVIC FLOOR REPAIR, the disclosures of which are hereby incorporated by reference.

FIELD OF THE INVENTION

The present invention relates to anchoring devices generally.

BACKGROUND OF THE INVENTION

Various types of anchoring devices are known for various applications.

SUMMARY OF THE INVENTION

The present invention seeks to provide an improved anchoring device.

There is thus provided in accordance with a preferred embodiment of the present invention an anchoring device including a finger-mountable work channel defining assembly defining a finger mounting axis and a work channel axis angled with respect to the finger mounting axis, the finger-mountable work channel defining assembly defining an aperture lying generally in an aperture plane angled with respect to the finger mounting axis and with respect to the work channel axis, an anchor insertion assembly arranged for limited axial displacement along the work channel axis with respect to the aperture so as to intersect the aperture plane and an anchor assembly including at least an anchoring portion and a flexible elongate portion attached thereto, the anchoring portion having a pre-anchoring operative orientation and an anchoring operative orientation.

There is also provided in accordance with another preferred embodiment of the present invention an anchoring device including a finger-mountable work channel defining assembly defining a finger mounting axis and a work channel axis angled with respect to the finger mounting axis, the finger-mountable work channel defining assembly defining an aperture lying generally in an aperture plane angled with respect to the finger mounting axis and with respect to the work channel axis, an anchor insertion assembly arranged for axial displacement along the work channel axis with respect to the aperture so as to intersect the aperture plane adjacent the aperture and an anchor assembly including at least an anchoring portion and a flexible elongate portion attached thereto, the anchoring portion having a pre-anchoring operative orientation and an anchoring operative orientation.

There is further provided in accordance with yet another preferred embodiment of the present invention an anchoring device including a finger-mountable work channel defining assembly defining a finger mounting axis and a work channel axis angled with respect to the finger mounting axis, the finger-mountable work channel defining assembly defining an aperture lying generally in an aperture plane angled with respect to the finger mounting axis and with respect to the work channel axis, an anchor insertion assembly arranged for axial displacement along the work channel axis with respect to the aperture so as to intersect the aperture plane adjacent the aperture and an anchor assembly including at least an anchoring portion and a flexible elongate portion attached thereto, having a pre-anchoring operative orientation and an anchoring operative orientation, the anchoring portion being displaceable along the work channel axis across the aperture plane by the anchor insertion assembly while in the pre-anchoring operative orientation.

There is yet further provided in accordance with still another preferred embodiment of the present invention an anchoring device including a finger-mountable work channel defining assembly defining a finger mounting axis and a work channel axis angled with respect to the finger mounting axis, the finger-mountable work channel defining assembly defining an aperture lying generally in an aperture plane angled with respect to the finger mounting axis and with respect to the work channel axis, the finger mounting axis lying in a finger mounting axis plane, the work channel axis lying in a work channel axis plane, which is parallel to the finger mounting axis plane and the aperture plane being orthogonal to the mutually parallel finger mounting axis plane and to the work channel axis plane, an anchor insertion assembly arranged for axial displacement along the work channel axis with respect to the aperture so as to intersect the aperture plane and an anchor assembly including at least an anchoring portion and a flexible elongate portion attached thereto.

There is still further provided in accordance with yet another preferred embodiment of the present invention an anchoring device including a finger-mountable work channel defining assembly defining a finger mounting axis and a work channel axis, the finger-mountable work channel defining assembly defining an aperture lying generally in an aperture plane angled with respect to the work channel axis, an anchor insertion assembly arranged for axial displacement along the work channel axis with respect to the aperture so as to intersect the aperture plane and an anchor assembly including at least an anchoring portion and a flexible elongate portion attached thereto.

There is also provided in accordance with yet another preferred embodiment of the present invention an anchoring device including a finger-mountable work channel defining assembly defining a finger mounting axis and a work channel axis, the finger-mountable work channel defining assembly defining a finger anchoring location engagement portion lying generally in an orientation angled with respect to the work channel axis, an anchor insertion assembly arranged for axial displacement along the work channel axis with respect to the engagement portion so as to engage the anchoring location adjacent the engagement portion and an anchor assembly including at least an anchoring portion and a flexible elongate portion attached thereto.

Preferably, the finger mounting axis lies in a finger mounting axis plane, the work channel axis lies in a work channel axis plane, which is parallel to the finger mounting axis plane and the aperture plane is orthogonal to the mutually parallel finger mounting axis plane and to the work channel axis plane.

In accordance with a preferred embodiment of the present invention the finger mountable work channel defining assembly is configured to be right or left hand specific. Additionally or alternatively, the finger mountable work channel defining assembly includes a finger mount element, an elongate work channel defining element and an insertion and stop defining element, which is fixedly mounted onto the elongate work channel defining element. Preferably, the finger mountable work channel defining assembly is formed as a single piece of a partially flexible plastic material and defines two side walls joined at an end wall and underside wall and is configured to enable an underside of the operator's finger to engage an anchoring site. Additionally or alternatively, the work channel defining assembly defines forward and rearward throughgoing fixed mounting channels for fixedly mounting of the elongate work channel defining element.

In accordance with a preferred embodiment of the present invention the work channel axis is angled with respect to the finger axis by 7 degrees. Additionally or alternatively, the work channel axis is angled with respect to the aperture plane by 40 degrees.

Preferably, the insertion and stop defining element is a hollow element including a generally cylindrical hollow portion which communicates with a hollow funnel-shaped portion defining an edge, which serves as a precise stop limiting the axial extent of displacement of the anchor insertion assembly therethrough.

In accordance with a preferred embodiment of the present invention the anchor insertion assembly includes first and second housing portions onto which are mounted an inner tube and button assembly including a button and an elongate tube fixedly mounted thereto at an end of the elongate tube. Additionally, the anchoring device also includes an outer tube and retainer assembly mounted onto the first and second housing portions. Preferably, the outer tube and retainer assembly includes a retaining disk, which is fixedly mounted onto an end of an elongate tube and a coil spring mounted over the elongate tube between the button and the retaining disk. Additionally, the anchoring device also includes a button guard element pivotably mounted onto the first and second housing portions for selectable protective engagement with the button.

In accordance with a preferred embodiment of the present invention the button is configured to have an engagement surface formed with a pair of retaining recesses arranged on opposite sides of a transverse slit and an axial bore, which extends therethrough and defines an aperture in the engagement surface at the transverse slit.

There is also provided in accordance with a preferred embodiment of the present invention a method for utilizing the anchoring device for positioning and inserting an anchoring assembly into an anchoring substrate, the method including inserting a finger of a user into the finger-mountable work channel defining assembly, whereby a distal phalanx of the finger is arranged so as to engage the anchoring substrate, and inserting the anchor insertion assembly into the finger-mountable work assembly with the anchor assembly preloaded therein, such that the orientation of the finger of the user precisely defines the location of anchoring engagement of the anchor assembly with the anchoring substrate.

Preferably, an extent of insertion of the anchor assembly in the anchoring substrate is precisely limited by engagement between the anchor insertion assembly and the finger-mountable work channel defining assembly.

BRIEF DESCRIPTION OF THE DRAWINGS

The present invention will be understood and appreciated more fully from the following detailed description in which.

DETAILED DESCRIPTION OF A PREFERRED EMBODIMENT

Figure 1A:
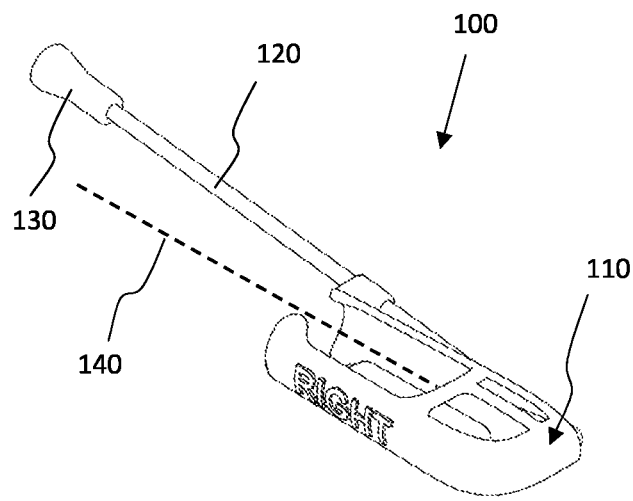
FIGS. 1A, 1B, 1C, 1D and 1E are respective simplified pictorial assembled view and exploded view, top view and bottom view illustrations as well as a simplified sectional view illustration, taken along lines E-E in FIG. 1C, of a right finger mountable work channel defining assembly, forming part of the anchoring device of an embodiment of the present invention.
Figure 1B:
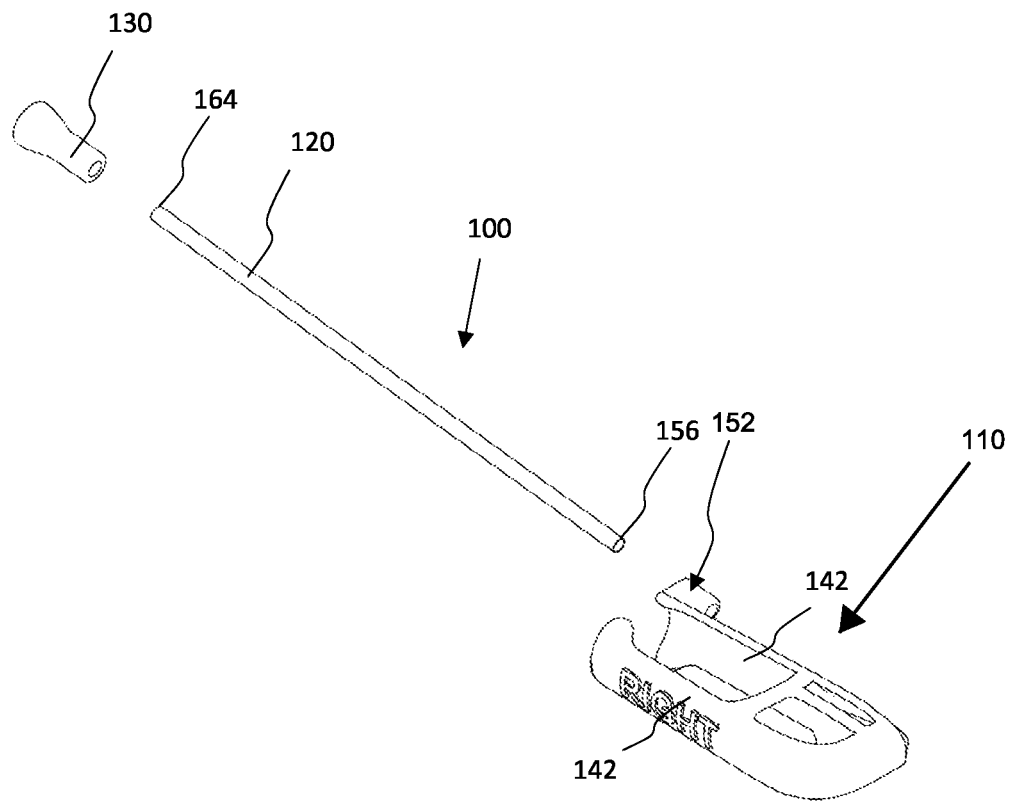
Figure 1C:
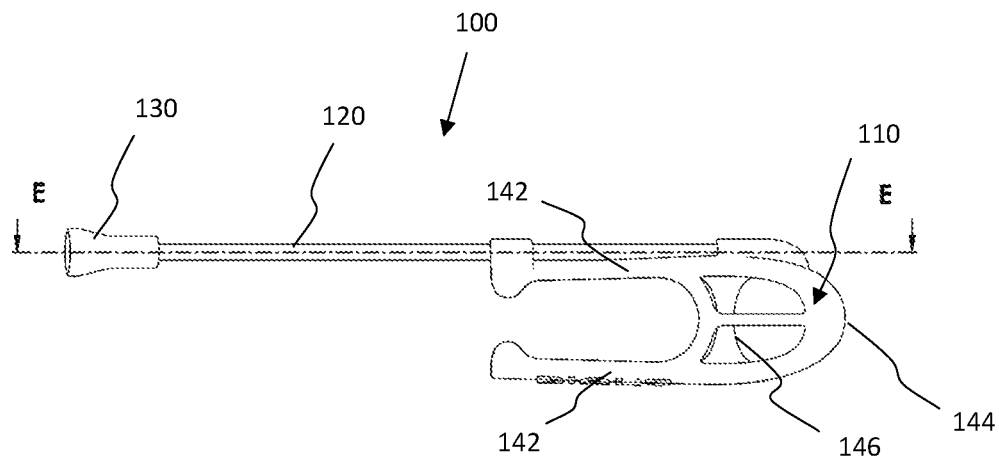

Reference is now made to FIGS. 1A, 1B, 1C, 1D and 1E, which are respective simplified pictorial assembled view and exploded view, top view and bottom view illustrations as well as a simplified sectional view illustration, taken along lines E-E in FIG. 1C, of a right finger mountable work channel defining assembly, forming part of an anchoring device of an embodiment of the present invention.

As seen in FIGS. 1A-1E, the right finger mountable work channel defining assembly, here designated by reference numeral 100, preferably comprises a finger mount element 110, an elongate work channel defining element 120, which is preferably fixedly mounted, at a first end thereof, onto the finger mount element 110, and an insertion and stop defining element 130, which is preferably fixedly mounted onto the elongate work channel defining element 120 at a second end thereof. The finger mount element 110, which is preferably configured to removably accommodate the right index finger of an operator, preferably is formed as a single piece of a partially flexible plastic material, such as polycarbonate, extending along a finger axis 140 and defines two side walls 142 preferably joined at an end wall 144 and an underside wall 146 and defining an opening 148 which is configured to enable an underside of the operator's finger, when fully inserted into the finger mount element 110, to be exposed and to engage a potential anchoring site. Opening 148 lies generally in an aperture plane 149.

Finger mount element 110 preferably also defines, at a first side wall 142 thereof, respective forward and rearward throughgoing fixed mounting channels 150 and 152 for fixedly mounting of elongate work channel defining element 120 thereto along an axis 154. As seen particularly in FIG. 1E, axis 154 is preferably angled with respect to the finger axis 140 by 7 degrees and to aperture plane 149 by 40 degrees.

Figure 1D:
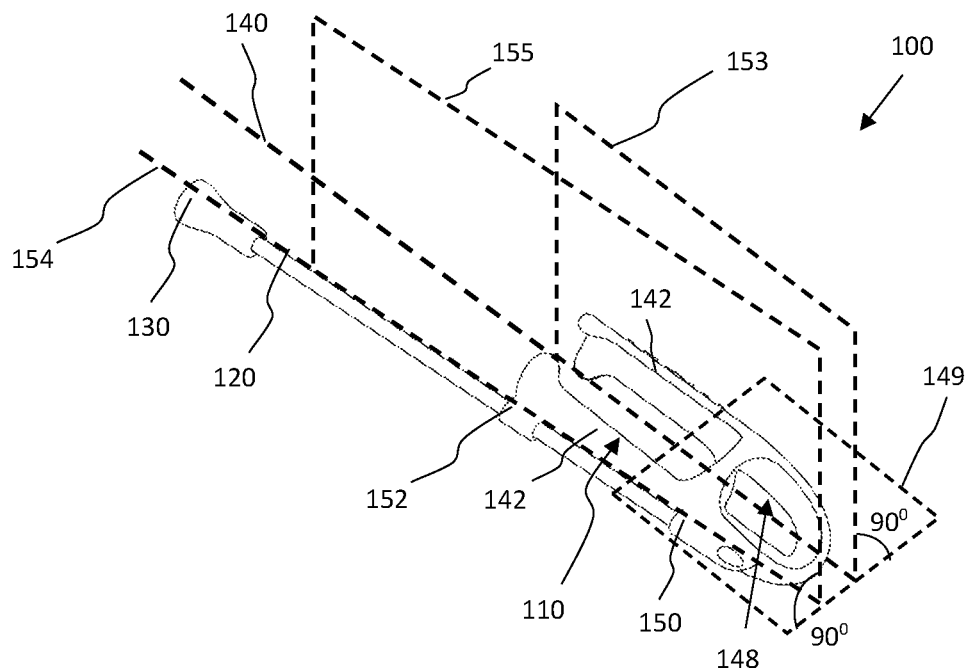
Figure 1E:
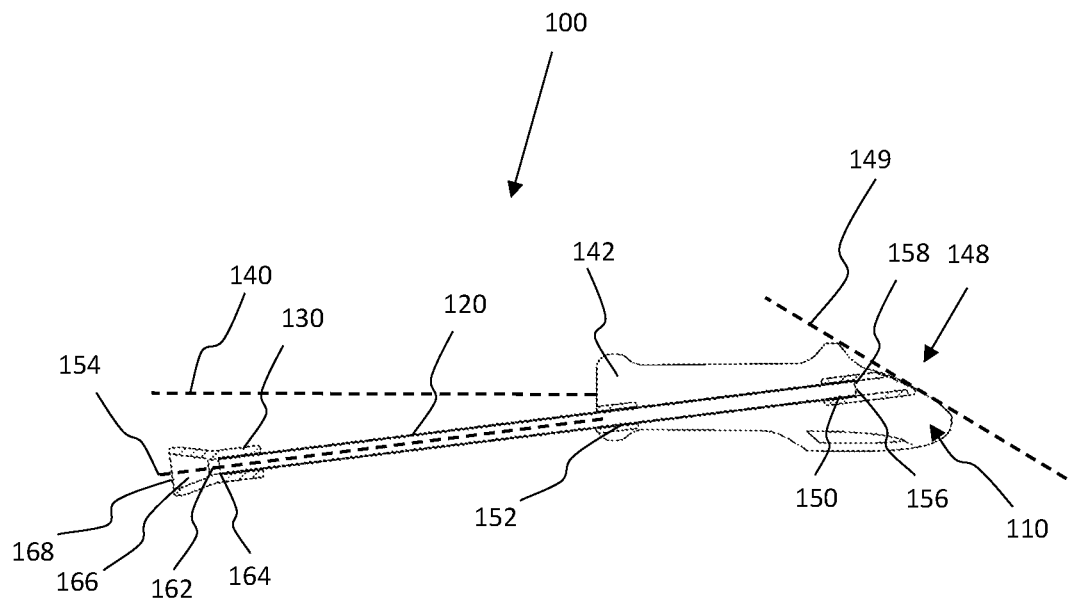

As seen particularly in FIG. 1D, it is a particular feature of an embodiment of the present invention that finger mounting axis 140 lies in a finger mounting axis plane 153 and the work channel axis 154 lies in a work channel axis plane 155, which is parallel to the finger mounting axis plane 153 and the aperture plane 149 is orthogonal to the mutually parallel finger mounting axis plane 153 and to the work channel axis plane 155.

Elongate work channel defining element 120 is preferably an elongate hollow tube, is preferably formed of stainless steel and preferably has an inner diameter of 2.6 mm and is fixed to the finger mount element 110 at channels 150 and 152 by a suitable adhesive. A first end 156 of elongate work channel defining element 120 is fixedly seated at a location 158 intermediate along channel 150.

Insertion and stop defining element 130 preferably is a hollow element including a generally cylindrical hollow portion 162 which accommodates a second end 164 of elongate work channel defining element 120, which is preferably fixed thereto by a suitable adhesive. Generally cylindrical hollow portion 162 preferably communicates with a hollow funnel-shaped portion 166, which defines an edge 168, which serves as a precise stop limiting the axial extent of displacement of the anchor insertion assembly therethrough.

Figure 2A:
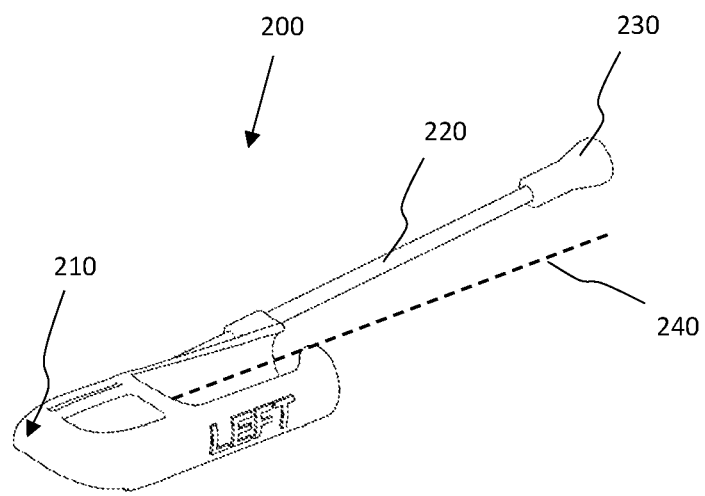
FIGS. 2A, 2B, 2C, 2D and 2E are respective simplified pictorial assembled view and exploded view, top view and bottom view illustrations as well as a simplified sectional view illustration, taken along lines E-E in FIG. 2C, of a left finger mountable work channel defining assembly, forming part of the anchoring device of an embodiment of the present invention.
Figure 2B:
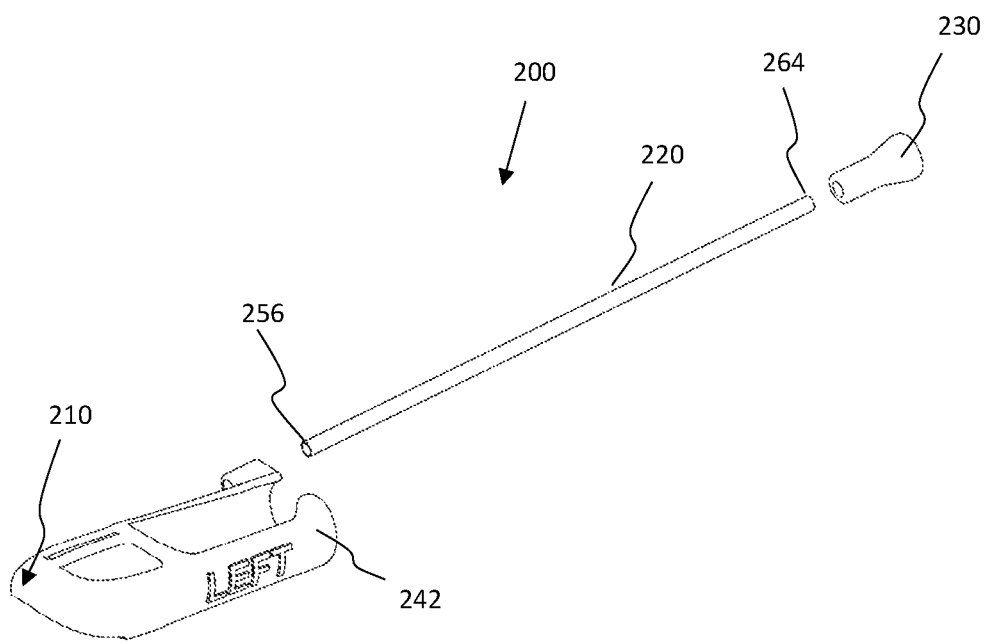
Figure 2C:
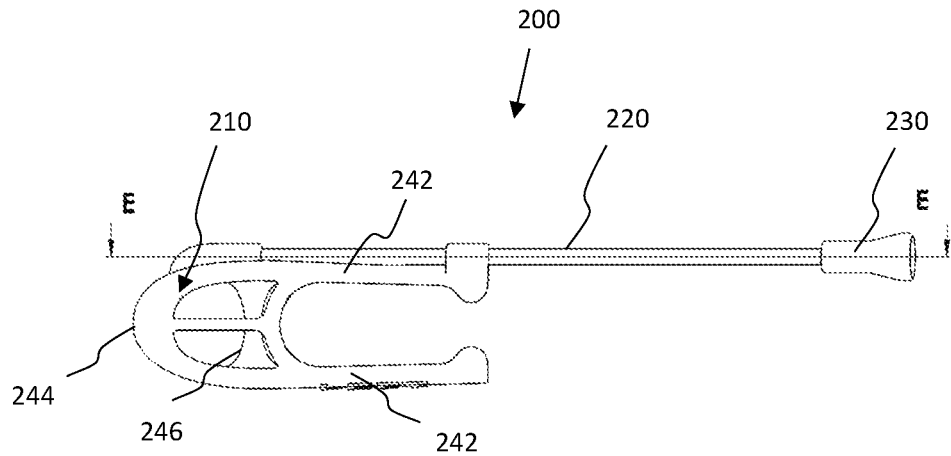

Reference is now made to FIGS. 2A, 2B, 2C, 2D and 2E, which are respective simplified pictorial assembled view and exploded view, top view and bottom view illustrations as well as a simplified sectional view illustration taken along lines E-E in FIG. 2C of a left finger mountable work channel defining assembly, forming part of the anchoring device of an embodiment of the present invention.

As seen in FIGS. 2A-2E, the left finger mountable work channel defining assembly, here designated by reference numeral 200, preferably comprises a finger mount element 210, an elongate work channel defining element 220, which is preferably fixedly mounted, at a first end thereof, onto the finger mount element 210 and an insertion and stop defining element 230, which is preferably fixedly mounted onto the elongate work channel defining element 220 at a second end thereof.

The finger mount element 210, which is preferably configured to removably accommodate the left index finger of an operator, preferably is formed as a single piece of a partially flexible plastic material, such as polycarbonate, extending along a finger axis 240 and defines two side walls 242 preferably joined at an end wall 244 and an underside wall 246 and defining an opening 248 which is configured to enable an underside of the operator's finger, when fully inserted into the finger mount element 210, to be exposed and to engage a potential anchoring site. Opening 248 lies generally in an aperture plane 249.

Finger mount element 210 preferably also defines, at a first side wall 242 thereof, respective forward and rearward throughgoing fixed mounting channels 250 and 252 for fixedly mounting of elongate work channel defining element 220 thereto along an axis 254. As seen particularly in FIG.

2E, axis 254 is preferably angled with respect to the finger axis 240 by 7 degrees and to aperture plane 249 by 40 degrees.

Figure 2D:
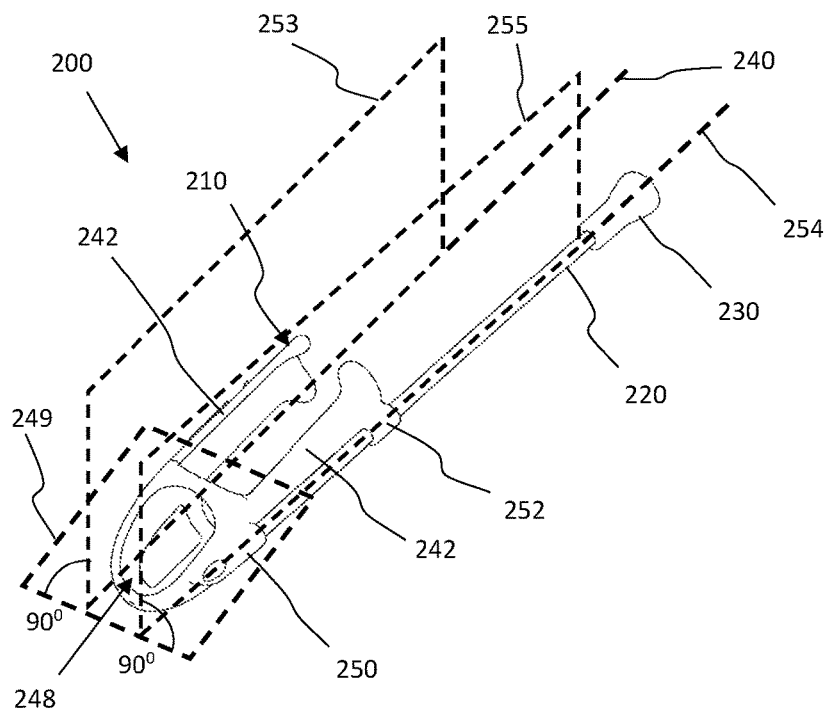
Figure 2E:
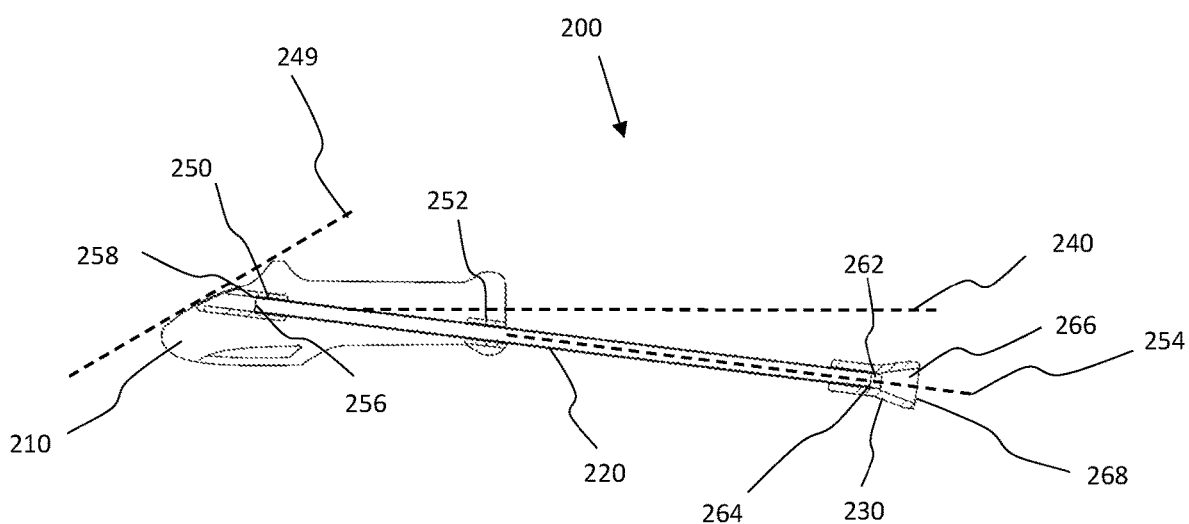

As seen particularly in FIG. 2D, it is a particular feature of an embodiment of the present invention that finger mounting axis 240 lies in a finger mounting axis plane 253 and the work channel axis 254 lies in a work channel axis plane 255, which is parallel to the finger mounting axis plane 253 and the aperture plane 249 is orthogonal to the mutually parallel finger mounting axis plane 253 and to the work channel axis plane 255.

Elongate work channel defining element 220 is preferably an elongate hollow tube is preferably formed of stainless steel and preferably has an inner diameter of 2.6 mm and is fixed to the finger mount element 210 at channels 250 and 252 by a suitable adhesive. A first end 256 of elongate work channel defining element 220 is fixedly seated at a location 258 intermediate along channel 250.

Insertion and stop defining element 230 preferably is a hollow element including a generally cylindrical hollow portion 262 which accommodates a second end 264 of elongate work channel defining element 220, which is preferably fixed thereto by a suitable adhesive. Generally cylindrical hollow portion 262 preferably communicates with a hollow funnel-shaped portion 266, which defines an edge 268, which serves as a precise stop limiting the axial extent of the anchor insertion assembly therethrough.

Reference is now made to FIGS. 3A, 3B, 3C and 3D, which are, respectively, a simplified pictorial assembled view, a simplified exploded view, a bottom view and a simplified sectional view illustrations of an anchor insertion assembly 300, forming part of the anchoring device of an embodiment of the present invention.

As seen in FIGS. 3A-3D, the anchor insertion assembly 300 preferably comprises first and second housing portions 310 and 320 onto which are mounted an inner tube and button assembly 330, including a button 332 and an elongate tube 334 fixedly mounted thereto at an end 336 of elongate tube 334, as by threading or adhesive. Also mounted onto first and second housing portions 310 and 320 and partially enclosing inner tube and button assembly 330 is an outer tube and retainer assembly 340 including a retaining disk 342 which is fixedly mounted onto an end 344 of an elongate tube 346. A coil spring 350 is mounted over elongate tube 334 between button 332 and retaining disk 342. A button guard element 360 is pivotably mounted onto first and second housing portions 310 and 320 for selectable protective engagement with button 332.

Figure 3A:
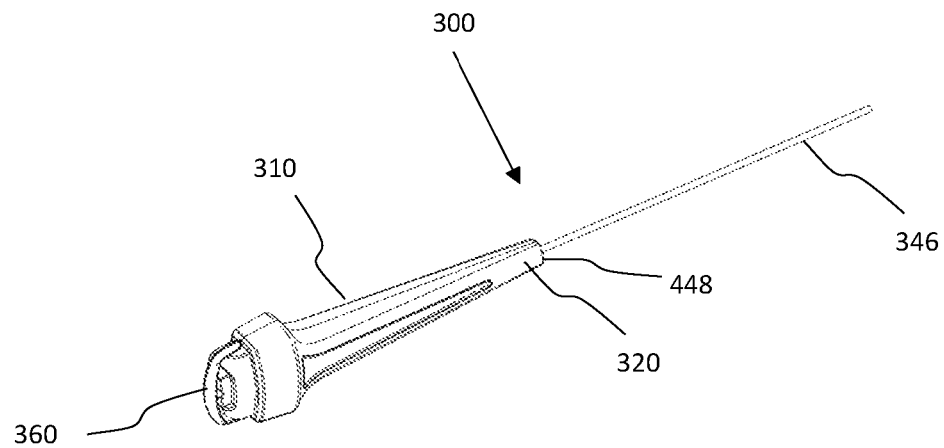
FIGS. 3A, 3B, 3C and 3D are, respectively, simplified pictorial assembled view, simplified exploded view and bottom view illustrations, as well as a simplified sectional view illustration, taken along lines D-D in FIG. 3C, of an anchor insertion assembly, forming part of the anchoring device of an embodiment of the present invention.
Figure 3B:
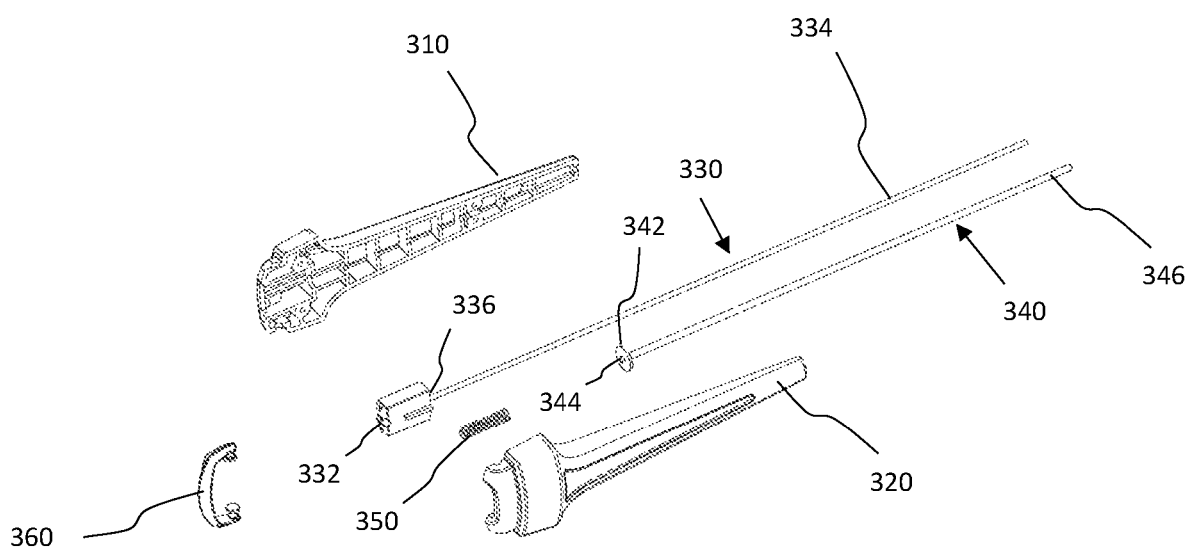
Figure 3C:
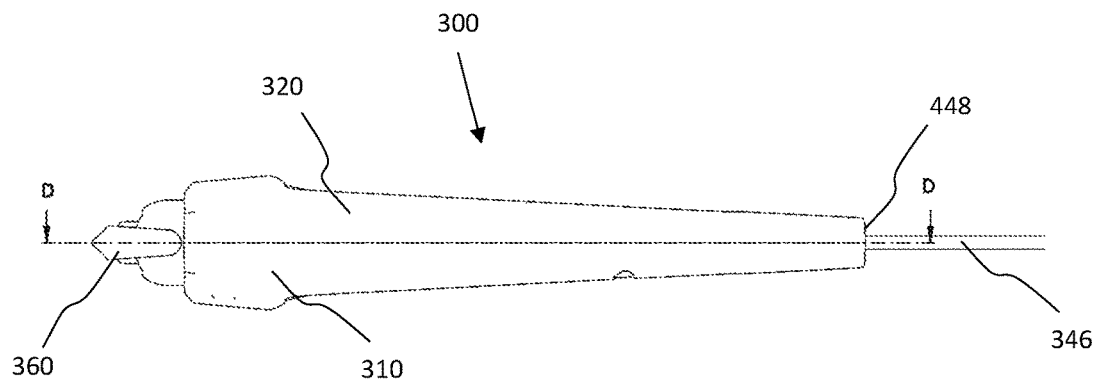
Figure 3D:
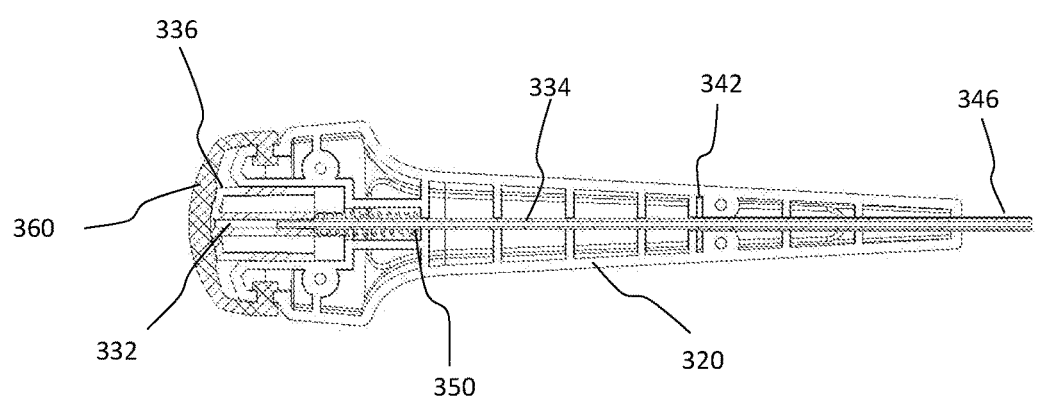
Figure 4A:
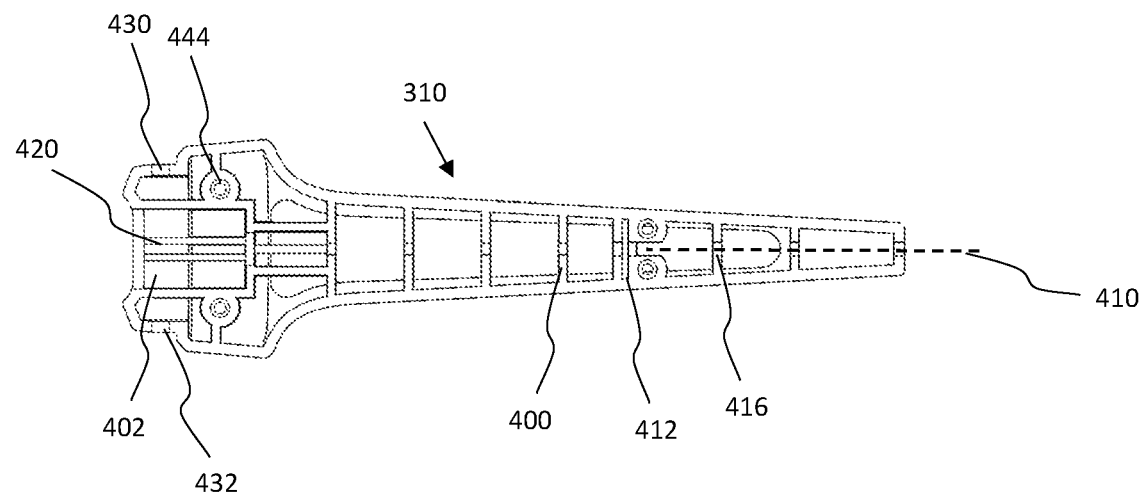
FIGS. 4A and 4B are simplified interior view illustrations of first and second housing portions of the anchor insertion assembly of FIGS. 3A-3D.
Figure 4B:
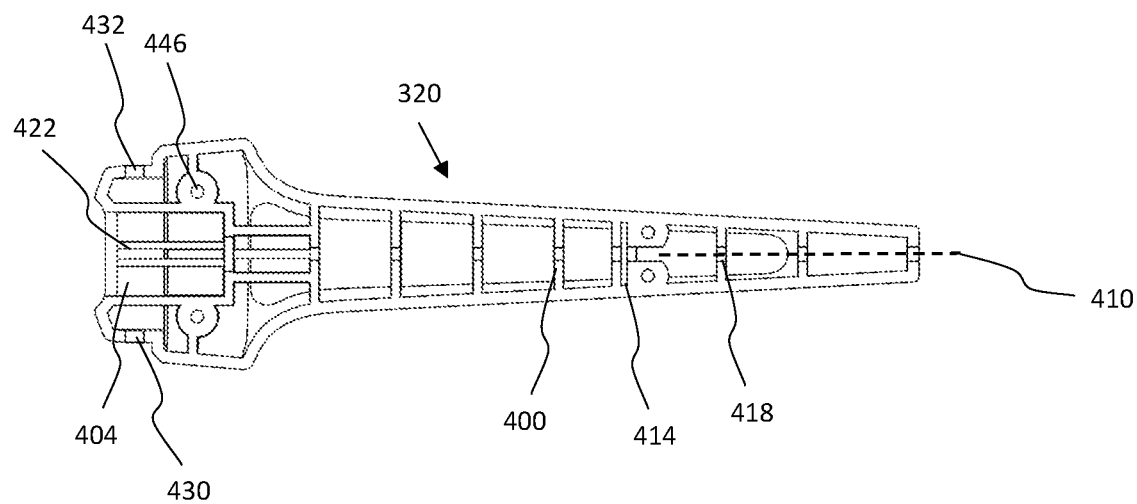
Figure 5A:
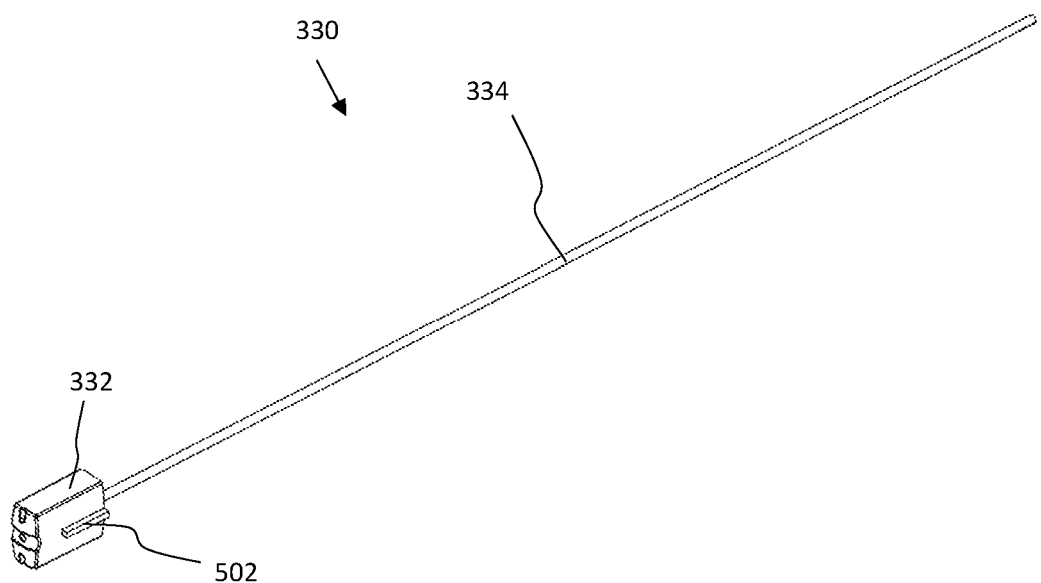
FIGS. 5A, 5B, 5C and 5D are, respectively, a simplified assembled view illustration, a simplified end view illustration, simplified side view illustration and a simplified sectional view illustration of an inner tube and button assembly forming part of the anchor insertion assembly of FIGS. 3A-3D, FIG. 5D being taken along lines D-D of FIG. 5C.
Figure 5B:
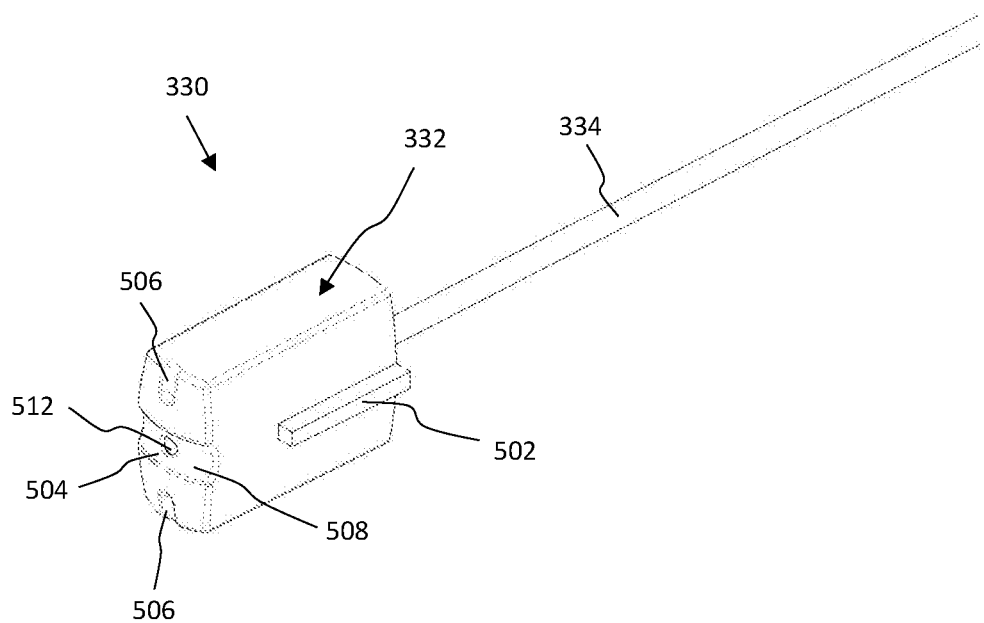
Figure 5C:
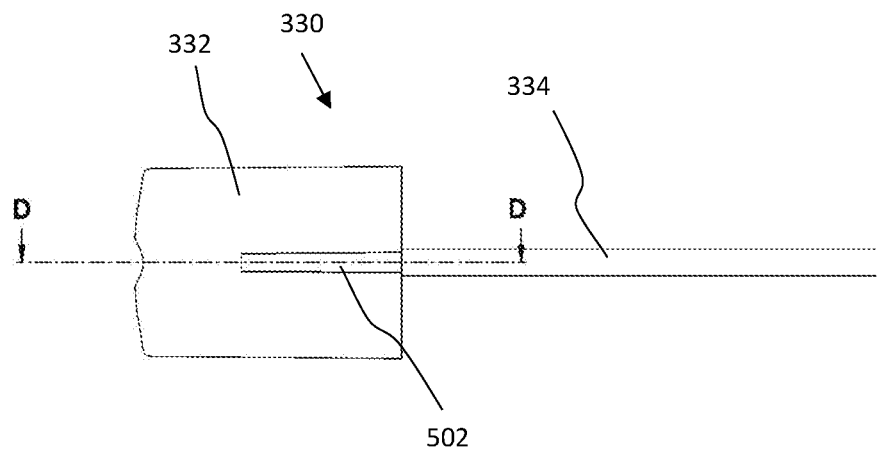
Figure 5D:
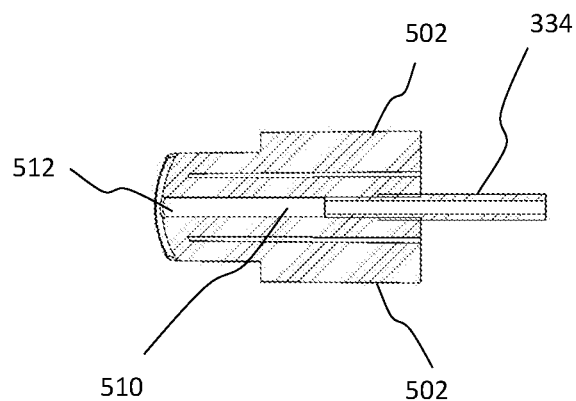

Reference is now made to FIGS. 4A and 4B, which are, respectively, simplified interior view illustrations of first and second housing portions 310 and 320 of the anchor insertion assembly 300 of FIGS. 3A-3D. As seen in FIGS. 4A and 4B, both first and second housing portions 310 and 320 include multiple structural internal ribs 400, which define, inter alia, respective sockets 402 and 404 for together accommodating button 332 and permitting limited axial translation thereof along an axis 410.

Ribs 400 in first and second housing portions 310 and 320 also define respective opposite sockets 412 and 414 for together accommodating button retaining disk 342 and not permitting axial translation thereof along axis 410. Ribs 400 in first and second housing portions 310 and 320 also define respective opposite cut-outs 416 and 418 for accommodating elongate tube 346 and respective opposite cut-outs 420 and 422 for accommodating button 332. First and second housing portions 310 and 320 together preferably also define a pair of pivot mount sockets 430 and 432.

First and second housing portions 310 and 320 may include respective screw sockets and channels 444 and 446 for receiving screws (not shown) which are employed for joining the first and second housing portions 310 and 320. Alternatively, first and second housing portions 310 and 320 may be joined together in other ways, such as by a snap-fit mechanism.

First and second housing portions 310 and 320 together define a forward-facing out end surface 448 (FIG. 3A).

Reference is now made to FIGS. 5A, 5B, 5C and 5D, which are, respectively, simplified assembled view, simplified end view, simplified side view and simplified sectional view illustrations of inner tube and button assembly 330 forming part of the anchor insertion assembly 300 of FIGS. 3A-3D and including button 332 and elongate tube 334.

It is seen that button 332 is a generally rectangular element having a pair of axial displacement guiding protrusions 502 on opposite side surfaces thereof, which are configured for slidable engagement with cut-outs 420 and 422. A rearwardly facing surface 504 of button 332 is preferably formed with a pair of retaining recesses 506 arranged on opposite sides of a transverse slit 508. Button 332 is formed with an axial bore 510 which extends therethrough and defines an aperture 512 in surface 504 at transverse slit 508. Elongate tube 334 preferably has an inner diameter of 1 mm and an outer diameter of 2 mm.

Figure 6A:
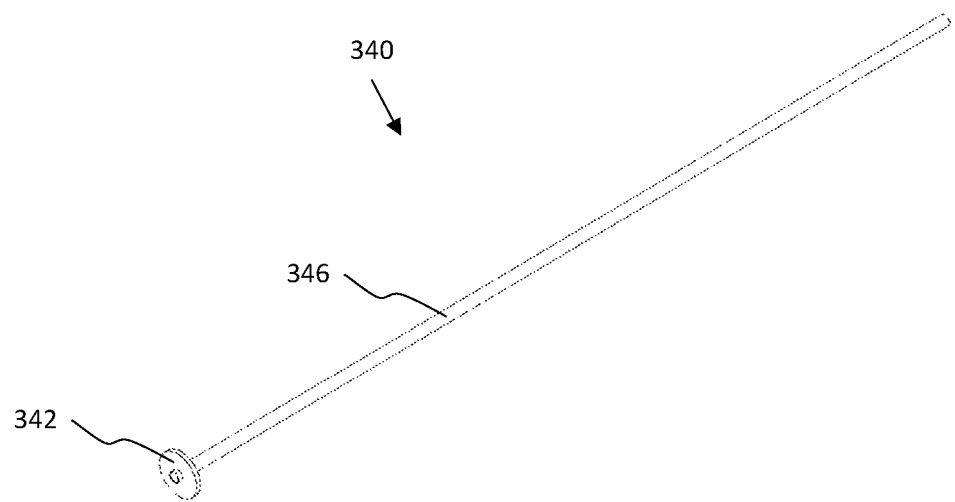
FIGS. 6A and 6B are respective simplified pictorial assembled view and exploded view illustrations of an outer tube and retainer assembly forming part of the anchor insertion assembly of FIGS. 3A-3D.
Figure 6B:
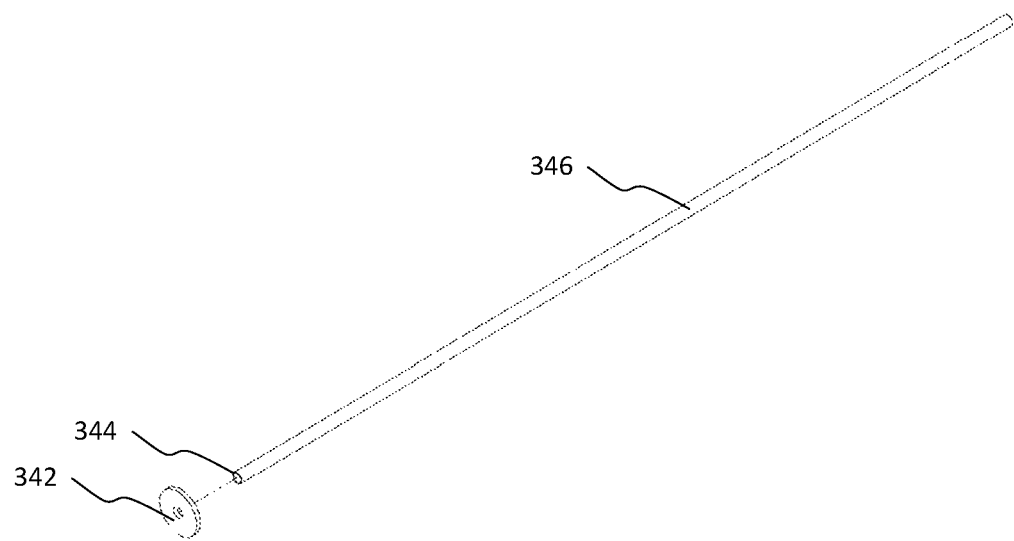

Reference is now made to FIGS. 6A and 6B, which are, respectively, a simplified assembled view illustration and a simplified exploded view illustration of outer tube and retainer assembly 340, including retaining disk 342, which is fixedly mounted onto end 344 of elongate tube 346, preferably by laser welding. Preferably, elongate tube 346 has an inner diameter slightly in excess of 2 mm for defining a clearance fit with elongate tube 334 and an outer diameter of 2.5 mm.

Figure 7A:
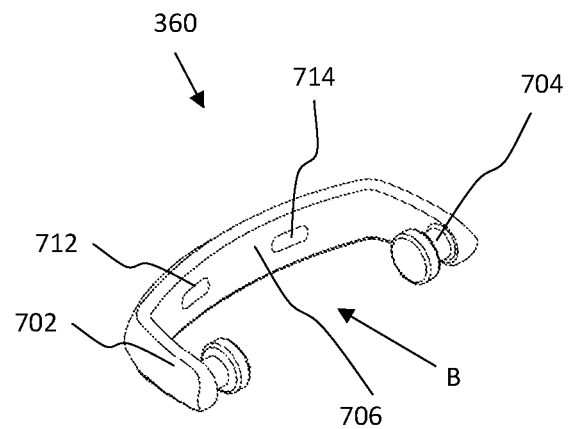
FIGS. 7A, 7B and 7C are, respectively, a simplified pictorial illustration, a simplified inner view illustration and a simplified sectional view illustration of a button guard element forming part of the anchor insertion assembly of FIGS. 3A-3D, FIG. 7B being taken in a direction indicated by an arrow B in FIG. 7A and FIG. 7C being taken along lines C-C of FIG. 7B.
Figure 7B:
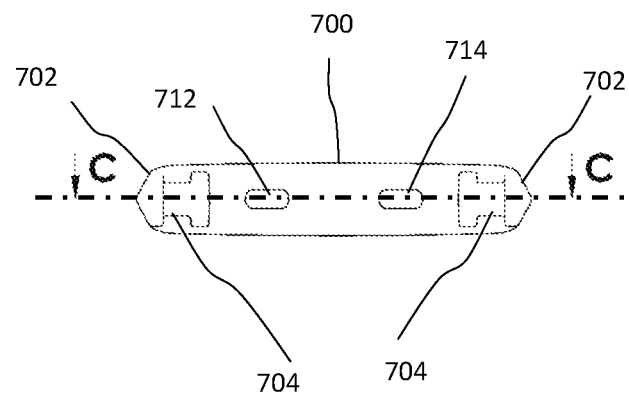
Figure 7C:
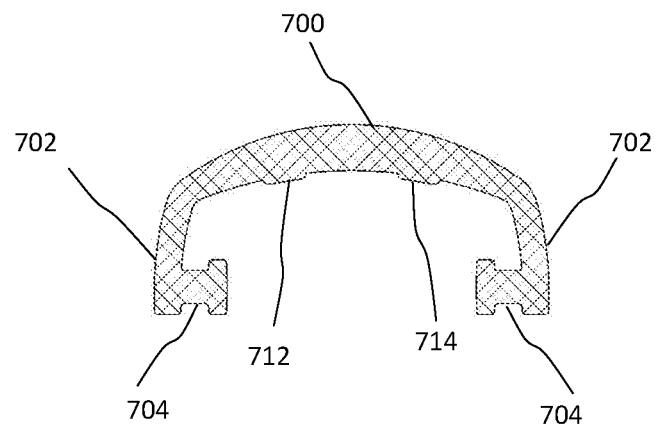

Reference is now made to FIGS. 7A, 7B and 7C, which are, respectively, a simplified pictorial illustration, a simplified inner view illustration and a simplified sectional view illustration of button guard element 360, forming part of the anchor insertion assembly 300 of FIGS. 3A-3D. As seen in FIGS. 7A-7C, button guard element 360 preferably defines an arch having a main portion 700 and a pair of legs 702, each of which is preferably formed with a pivot mount protrusion 704, which engages a corresponding one of pivot mount socket 430 and 432. An underside surface 706 of main portion 700 preferably defines a pair of engagement protrusions 712 and 714 for pivotably removable engagement with corresponding retaining recesses 506 of button 332.

Figure 8A:
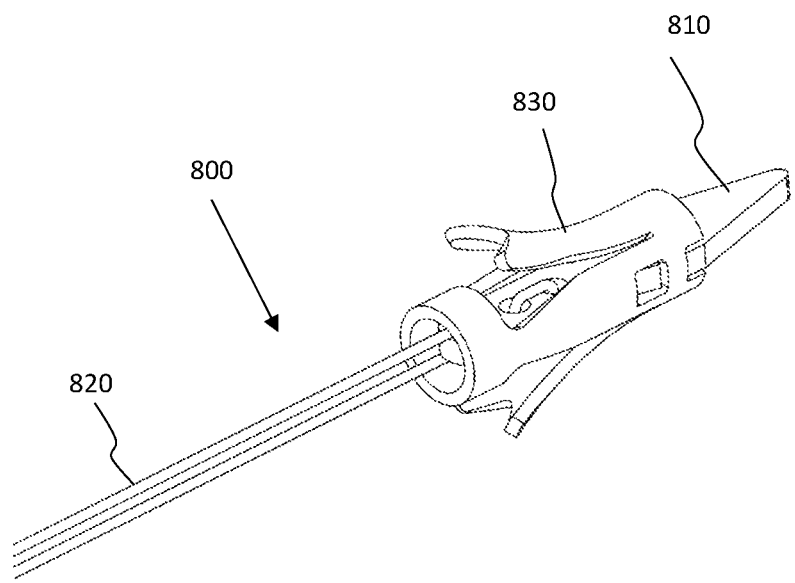
FIGS. 8A, 8B, 8C and 8D are respective simplified pictorial assembled view, exploded view and top view illustrations, as well as a sectional view illustration taken along lines D-D in FIG. 8C of an anchor assembly, forming part of the anchoring device of an embodiment of the present invention, in a non-compressed state.
Figure 8B:
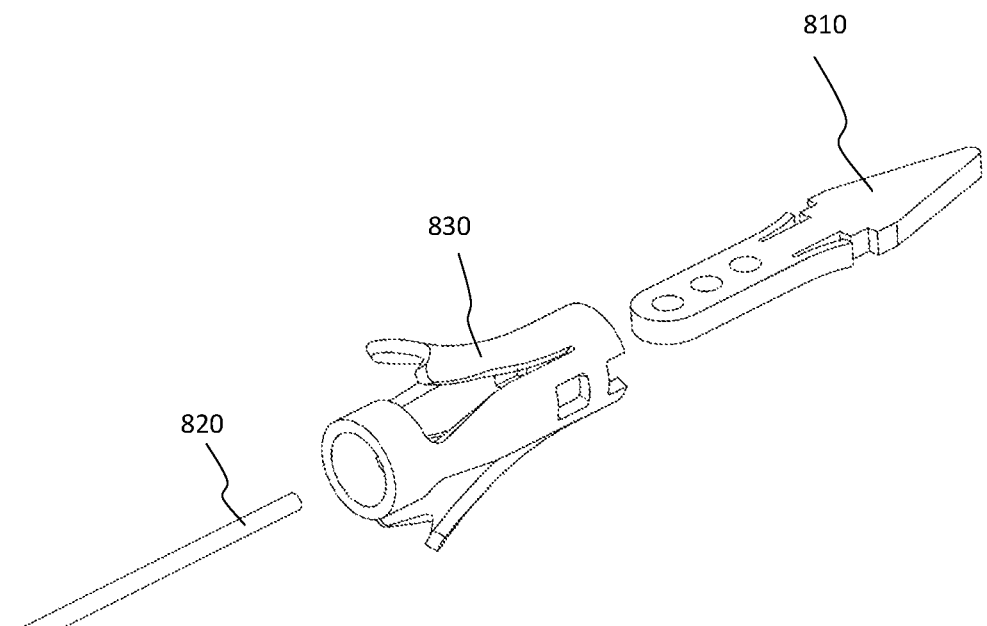
Figure 8C:
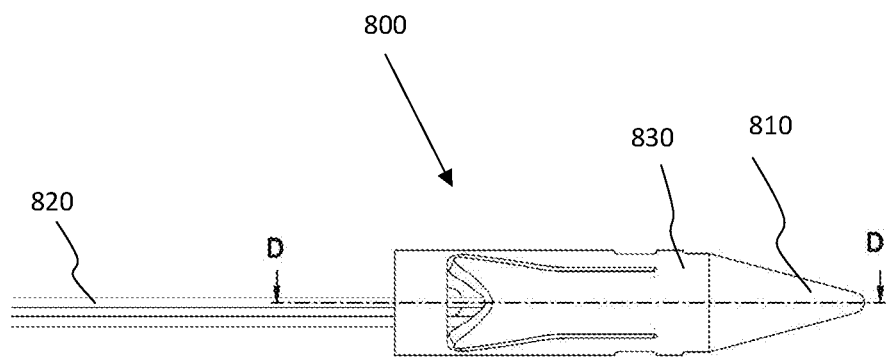
Figure 8D:
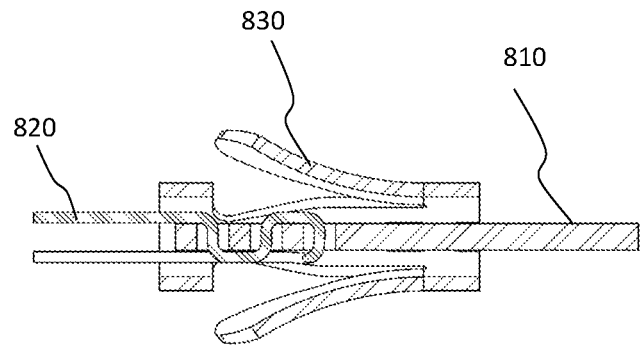

Reference is now made to FIGS. 8A, 8B, 8C and 8D, which are respective simplified pictorial assembled view, exploded view and top view illustrations, as well as a sectional view, illustration, taken along lines D-D in FIG. 8C, of an anchor assembly 800, forming part of the anchoring device of an embodiment of the present invention, in a non-compressed state. As seen in FIGS. 8A-8D, the anchor assembly 800 includes a penetrating element 810, which is coupled to a flexible elongate element 820, such as a suture, and an anchoring element 830, which preferably has two operative orientations, a non-compressed state, defining a pre-anchoring operative orientation, and a compressed state, defining an anchoring operative orientation.

Figure 9:
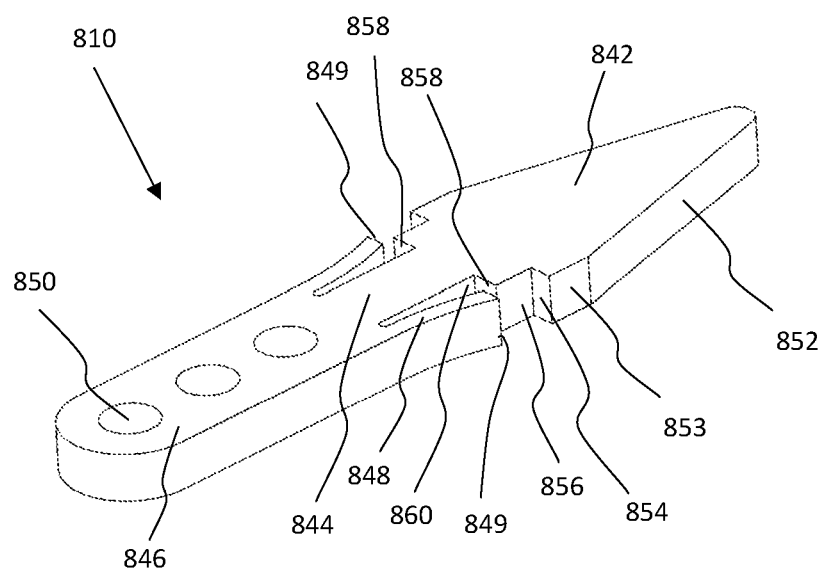
FIG. 9 is a simplified illustration of a penetrating element forming part of the anchor assembly of FIGS. 8A-8D.
Figure 10A:
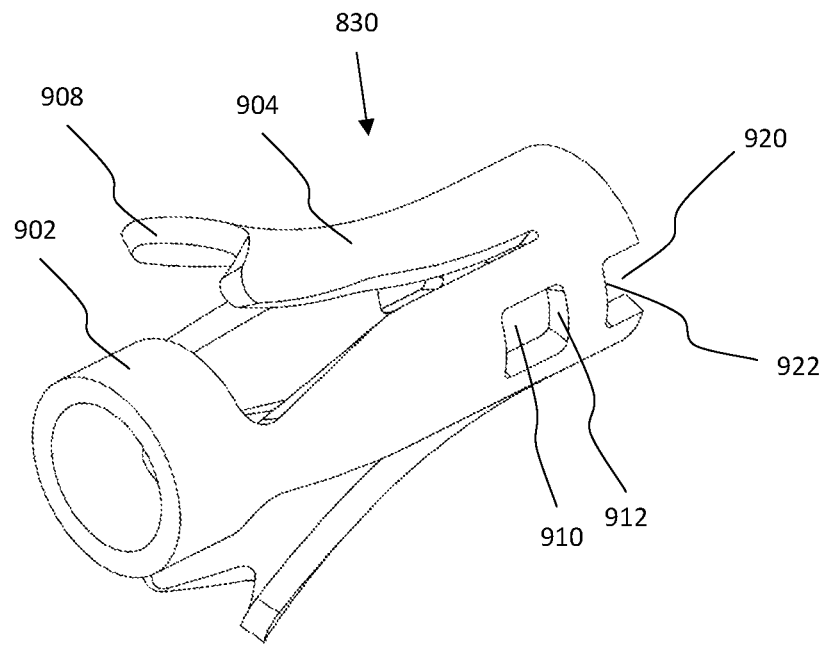
FIGS. 10A, 10B, 10C and 10D are, respectively, a simplified pictorial illustration, a simplified top view illustration, a simplified sectional view illustration and a simplified side view illustration of an anchoring element forming part of the anchor assembly of FIGS. 8A-8D in a non-compressed state, FIG. 10C being taken along lines C-C of FIG. 10B.
Figure 10B:
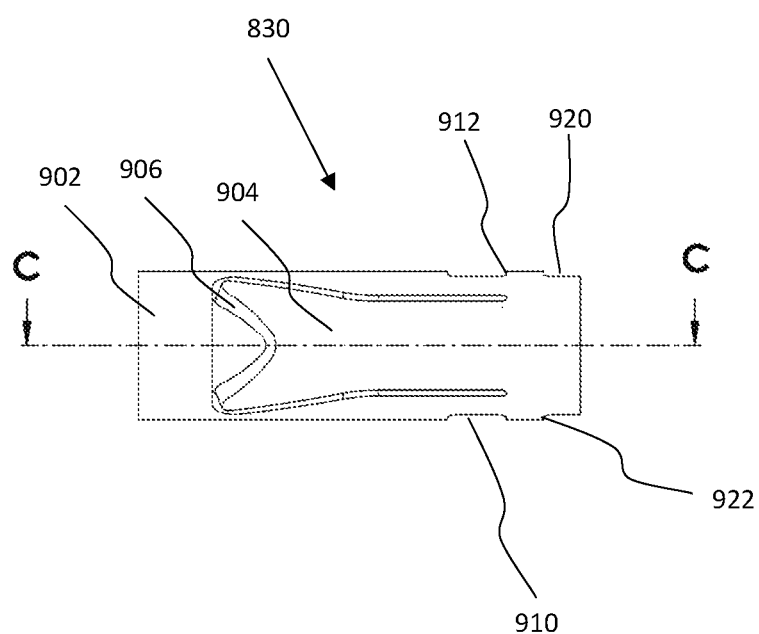
Figure 10C:
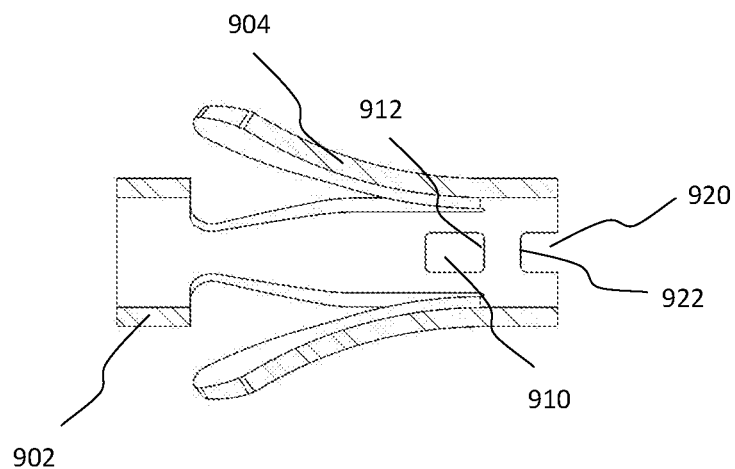
Figure 10D:
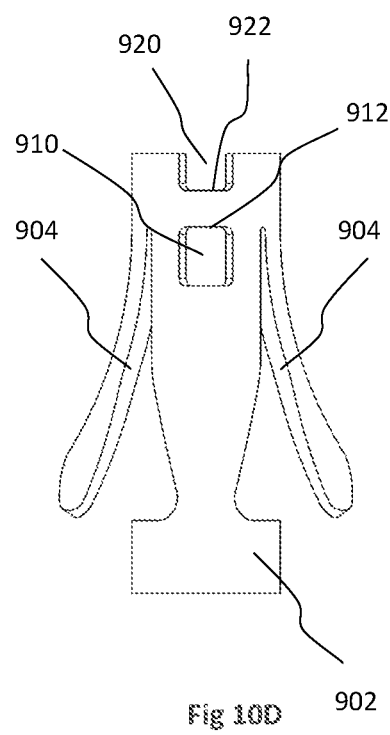
Figure 11A:
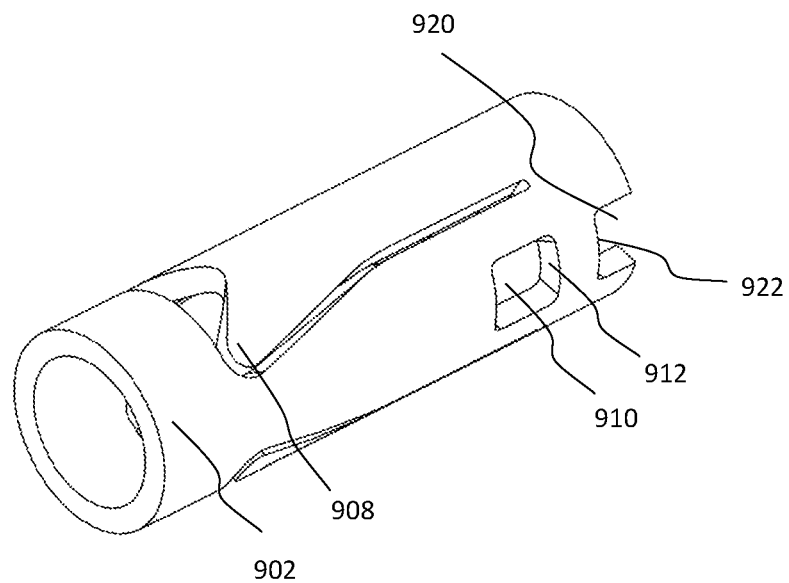
FIGS. 11A, 11B, 11C and 11D are, respectively, a simplified pictorial illustration, a simplified top view illustration, a simplified sectional view illustration and a simplified side view illustration of the anchoring element of FIGS. 10A-10D in a compressed state, FIG. 11C being taken along lines C-C of FIG. 11B.
Figure 11B:
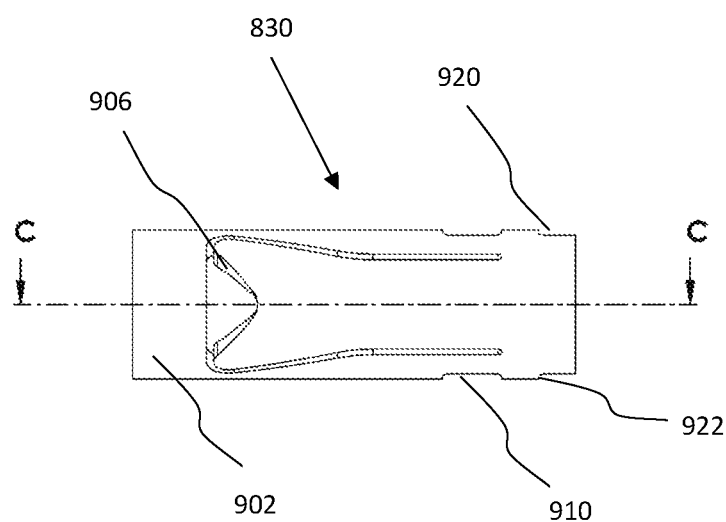
Figure 11C:
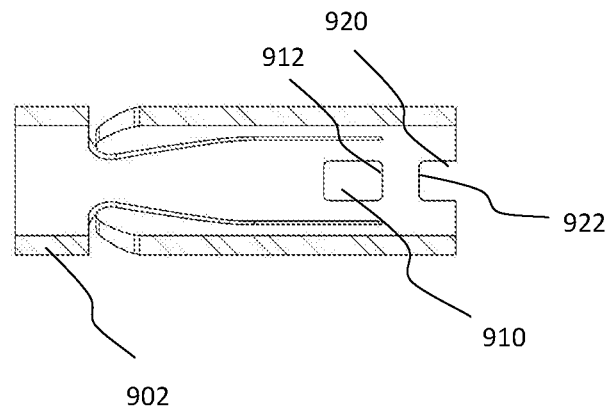
Figure 11D:
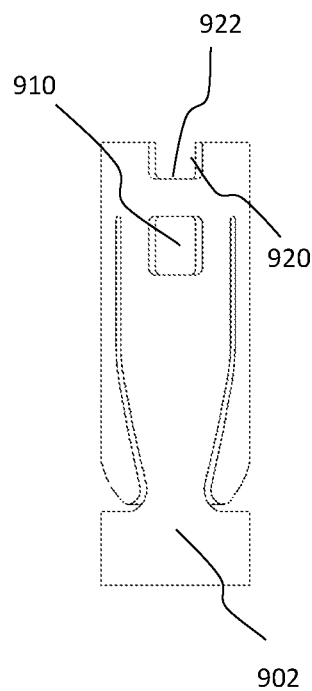

Reference is now made to FIG. 9, which is a simplified illustration of penetrating element 810. As seen in FIG. 9, penetrating element 810, which is preferably formed of Nitinol, includes a pointed forward portion 842, a neck portion 844 and a rearward engagement portion 846. Rearward engagement portion 846 preferably includes a pair of flexible retaining fingers 848, having end edge surfaces 849, and a plurality of apertures 850 for threaded engagement therewith of flexible elongate element 820. Adjacent and forwardly of neck portion 844, penetrating element 810 preferably defines a plurality of pairs of engagement side edge surfaces including a pair of forwardmost tapered edge surfaces 852 and a pair of intermediate tapered edge surfaces 853, rearwardly terminating in a pair of transverse edge surfaces 854, rearwardly terminating in a pair of axial edge surfaces 856, rearwardly terminating in a further pair of transverse edge surfaces 858, rearwardly terminating in a further pair of axial edge surfaces 860 which lie inwardly of respective flexible retaining fingers 848.

Reference is now made to FIGS. 10A, 10B, 10C and 10D, which are, respectively, a simplified pictorial illustration, a simplified top view illustration, a simplified sectional view illustration and a simplified side view illustration of anchoring element 830 forming part of the anchor assembly of FIGS. 8A-8D in a non-compressed state, and to FIGS. 11A, 11B, 11C and 11D, which are, respectively, a simplified pictorial illustration, a simplified top view illustration, a simplified sectional view illustration and a simplified side view illustration of anchoring element 830 in a compressed state.

As seen in FIGS. 10A-11D, anchoring element 830, which is preferably formed of Nitinol, is a generally hollow cylindrical element, particularly when in a compressed state. Anchoring element 830 preferably comprises a rearward ring portion 902 forward of which there are provided a pair of mutually azimuthally oppositely arranged rearwardly opening flaps 904, which are normally outwardly extending but can be squeezed inwardly to a compressed state. Each flap preferably defines a rearwardly facing edge surface 906, each of which defines a pair of flap feet 908. Flaps 904 are preferably defined by flap outline cuts in the generally hollow cylindrical element which defines anchoring element 830.

Azimuthally orthogonally to flaps 904 adjacent a forward portion of anchoring element 830 there are preferably formed a pair of mutually azimuthally oppositely arranged retaining apertures 910, each having a rearward facing edge surface 912, which are arranged for engagement therewith of flexible retaining fingers 848 of penetrating element 810. Forward of each of apertures 910, there is preferably formed a cut out 920. Cut out 920 has a forward facing surface 922 for accommodating forwardmost tapered edge surfaces 852 and transverse edge surfaces 854 of penetrating element 810.

Figure 12A:
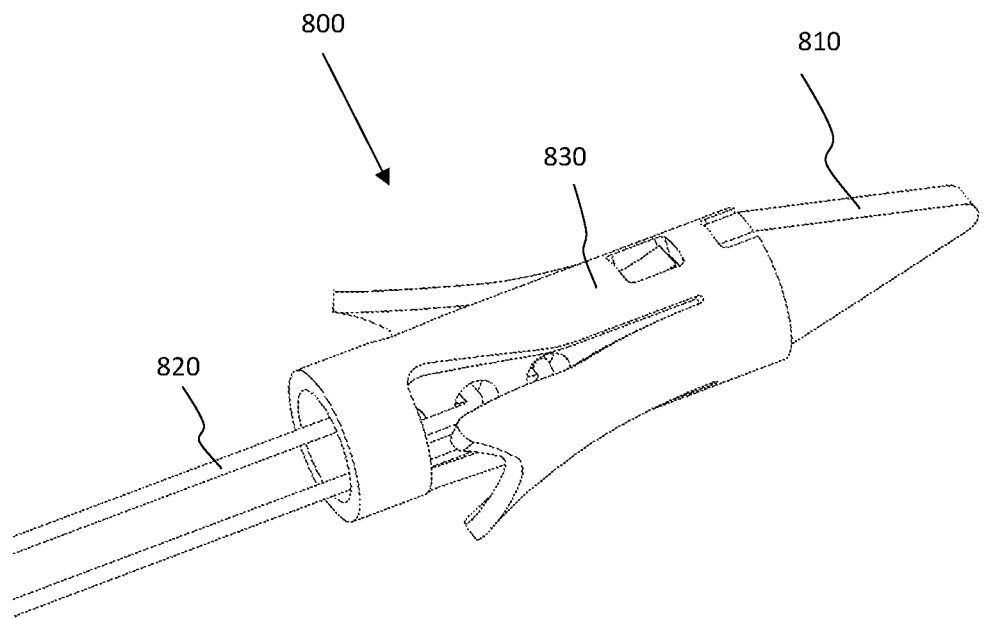
FIGS. 12A, 12B, 12C and 12D are respective simplified pictorial assembled view, exploded view and side view illustrations, as well as a sectional view illustration, taken along lines D-D in FIG. 12C, of the anchor assembly of FIGS. 8A-11D, in an non-compressed state.
Figure 12B:
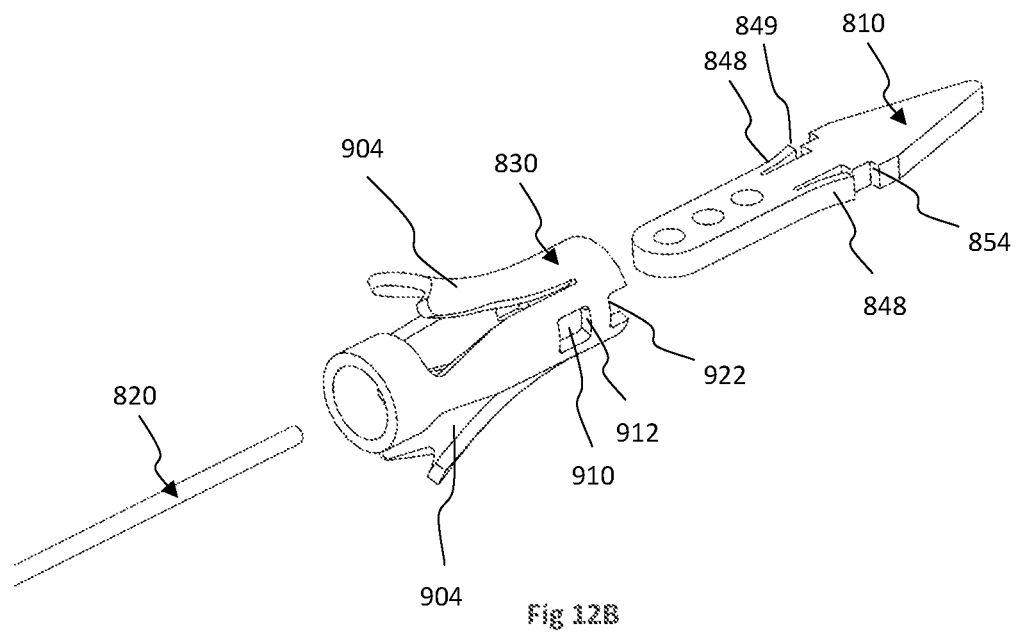
Figure 12C:
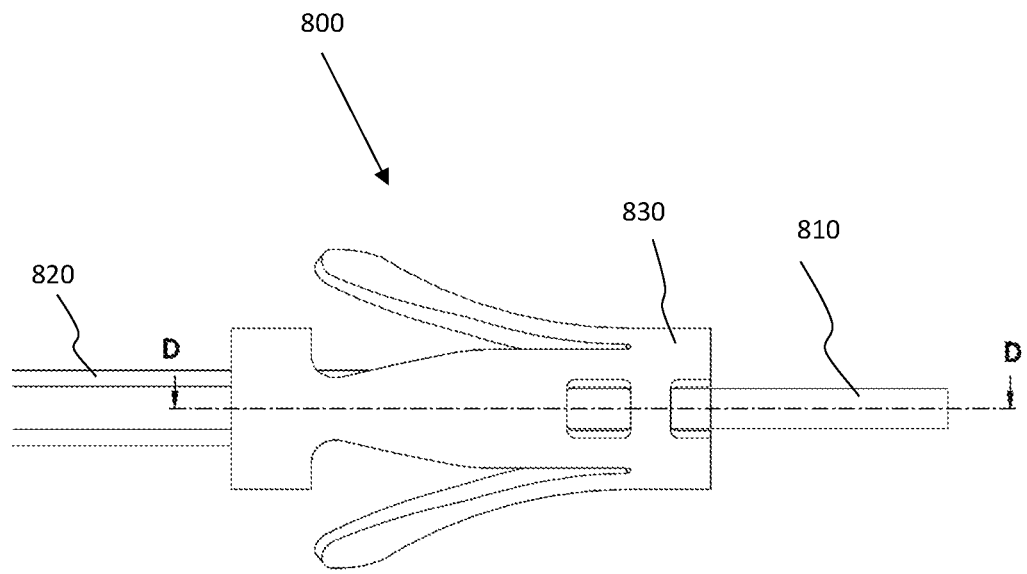
Figure 12D:
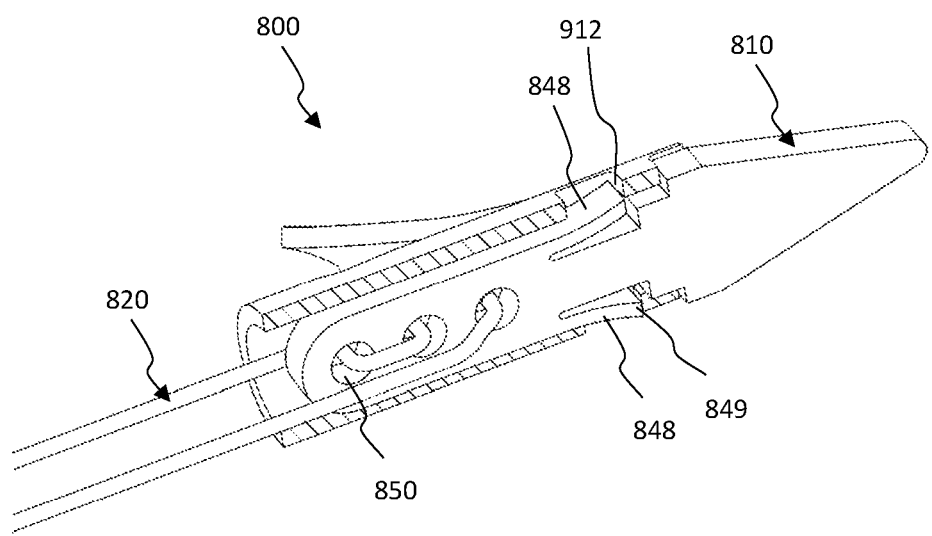
Figure 12E:
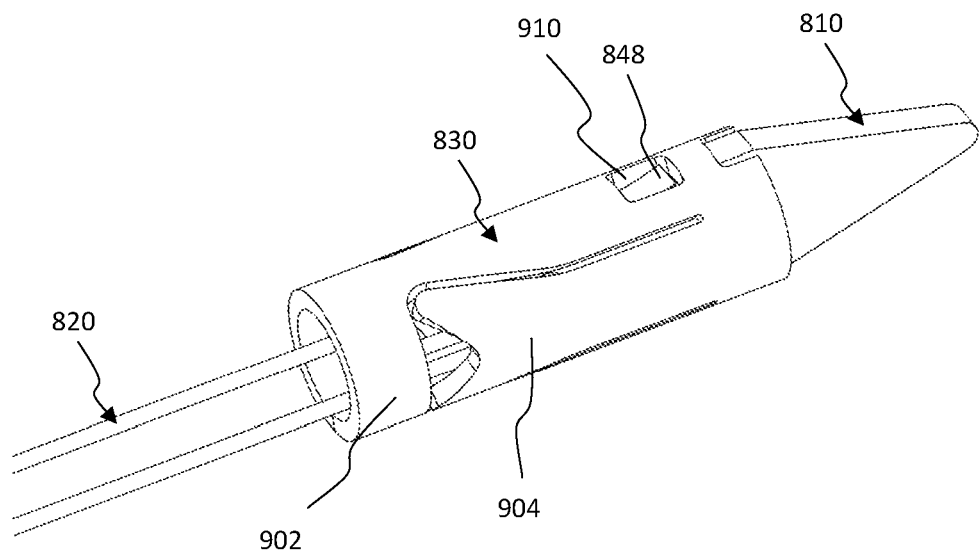
FIGS. 12E, 12F, 12G and 12H are respective simplified pictorial assembled view, exploded view and side view illustrations, as well as a sectional view illustration, taken along lines H-H in FIG. 12G, of the anchor assembly of FIGS. 8A-12D, in a compressed state.
Figure 12F:
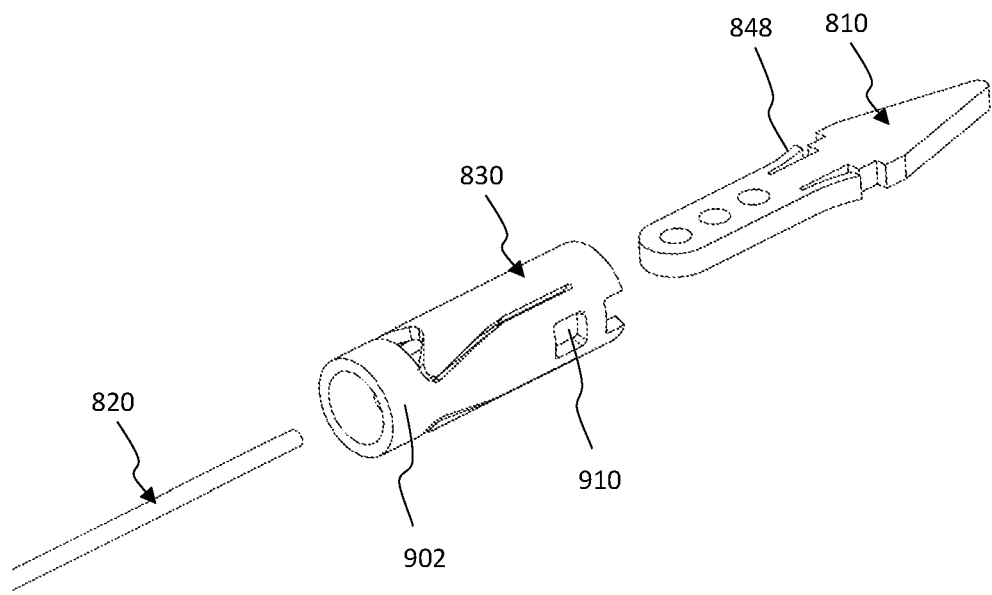

Reference is now made to FIGS. 12A, 12B, 12C and 12D, which are respective simplified pictorial assembled view, exploded view and side view illustrations as well as a sectional view illustration, taken along lines D-D in FIG. 12C, of the anchor assembly 800 of FIGS. 8A-11D in an non-compressed state. As noted above with reference to FIGS. 8A-8D, the anchor assembly 800 includes penetrating element 810, which is coupled to flexible elongate element 820, such as a suture, and anchoring element 830.

As seen in a non-compressed state in FIGS. 12A-12D, as well as in FIGS. 8A-8D, flexible elongate element 820 of the anchor assembly 800 is threaded through apertures 850 in penetrating element 810 and the anchoring element 830 is snap-fitted over the penetrating element 810. The anchoring element 830 is retained in engagement with the penetrating element 810 by engagement of flexible retaining fingers 848 of penetrating element 810 with apertures 910 of the anchoring element 830, such that end edge surfaces 849 engage corresponding facing aperture edge surfaces 912 of apertures 910 of the anchoring element 830 and by engagement of transverse surfaces 854 of penetrating element 810 with forward facing edge surfaces 922.

When in the non-compressed state shown in FIGS. 12A-12D, rearwardly opening flaps 904 of anchoring element 830 extend outwardly as shown. The flexible elongate element 820, which is effectively folded over by its engagement with penetrating element 810, extends rearwardly as two filaments, from penetrating element 810 and anchoring element 830 through rearward ring portion 902 of anchoring element 830.

Figure 12G:
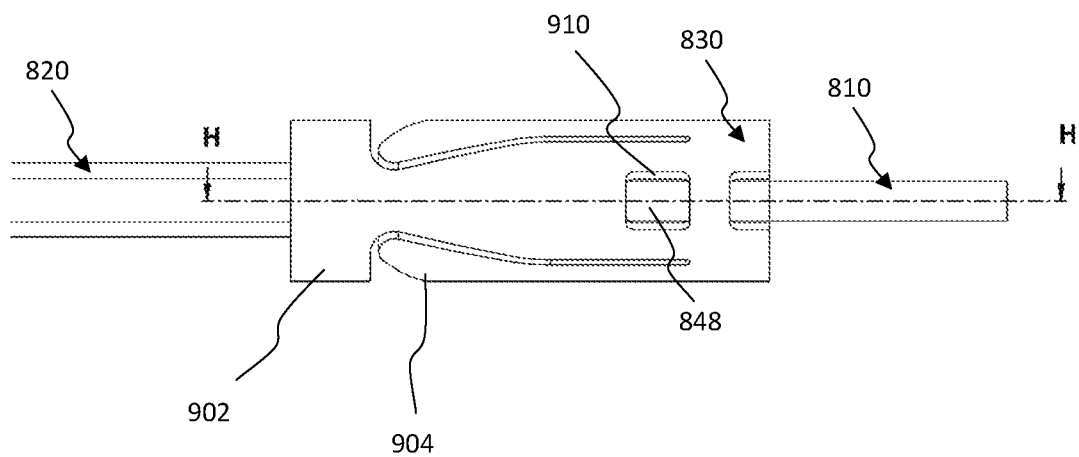
Figure 12H:
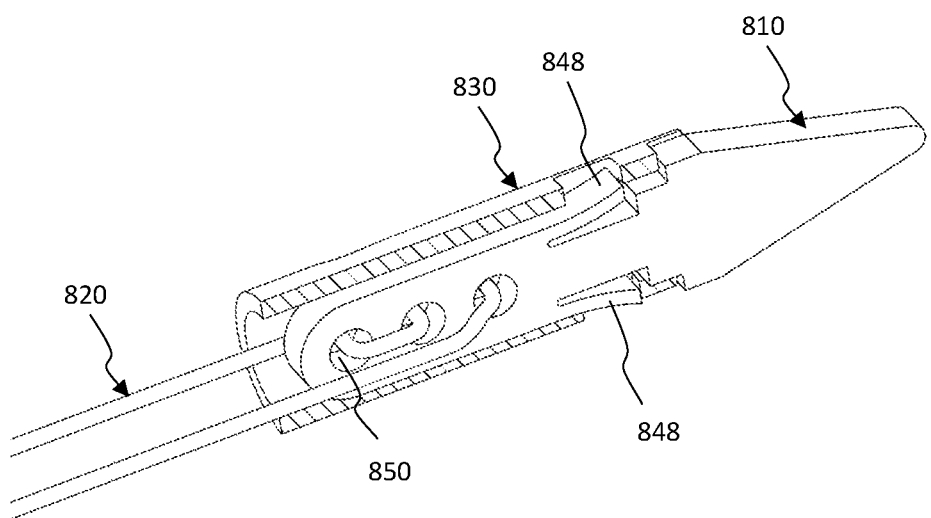

Reference is now made to FIGS. 12E, 12F, 12G and 12H, which are respective simplified pictorial assembled view, exploded view and side view illustrations, as well as a sectional view illustration, taken along lines H-H in FIG. 12G, of the anchor assembly 800 of FIGS. 8A-12D, in a compressed state. As seen by comparing FIGS. 12E-12H to FIGS. 12A-12D, it is seen that when in a compressed state, such as when retained at a forward end of elongate tube 346 of the anchor insertion assembly 300, rearwardly opening flaps 904 of anchoring element 830 are forced inwardly into a generally cylindrical orientation together with the remainder of the anchoring element 830, including rearward ring portion 902 thereof.

Figure 13A:
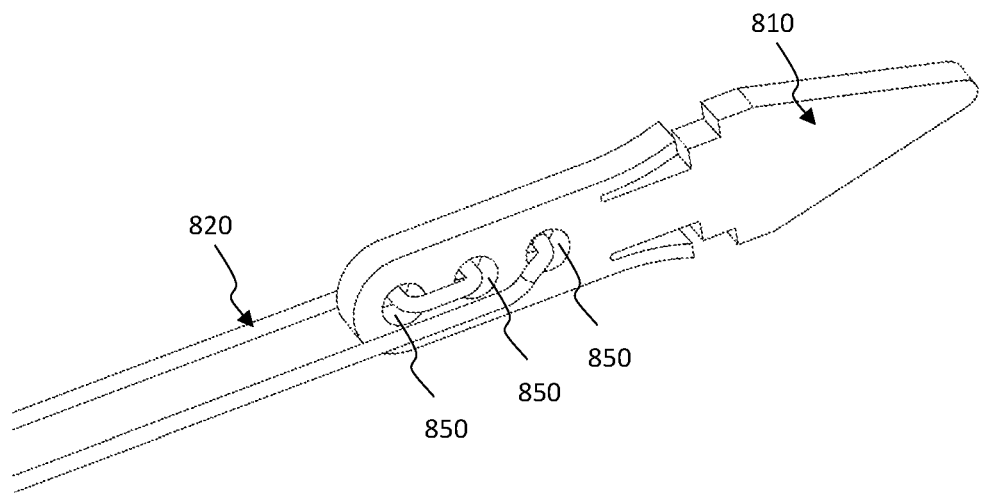
FIGS. 13A, 13B and 13C are simplified respective pictorial view, side view and sectional illustrations of one stage in the assembly of the anchor assembly of FIGS. 8A-12D, FIG. 13C being taken along lines C-C in FIG. 13B.
Figure 13B:
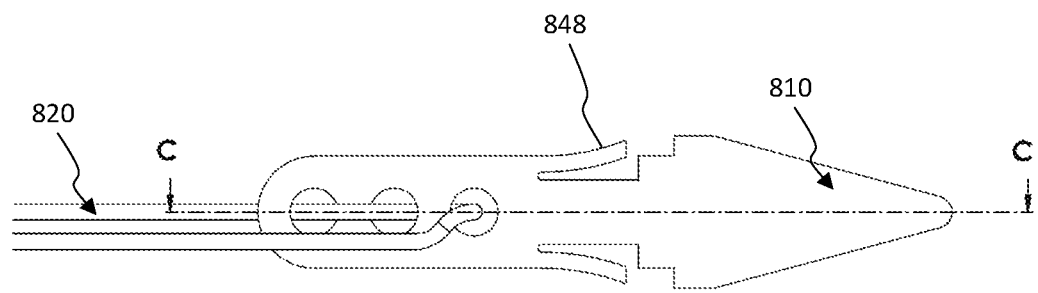
Figure 13C:
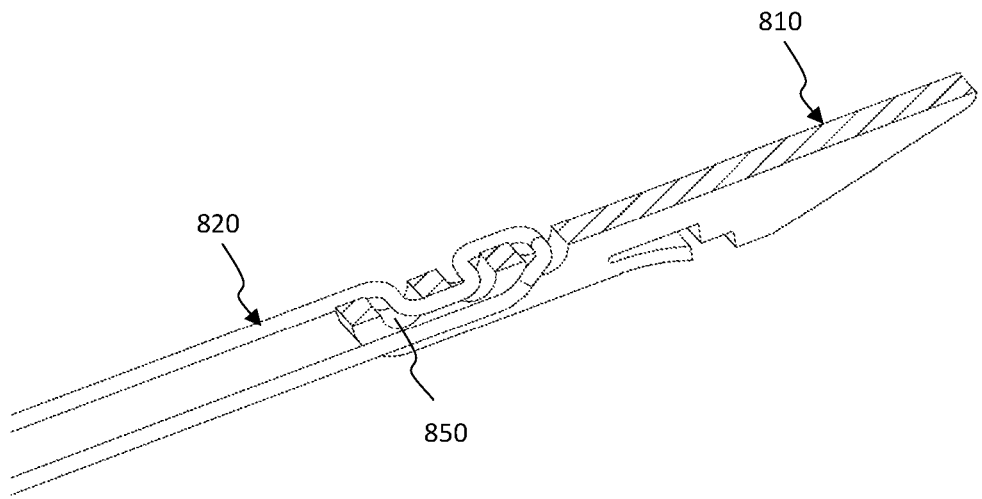
Figure 14A:
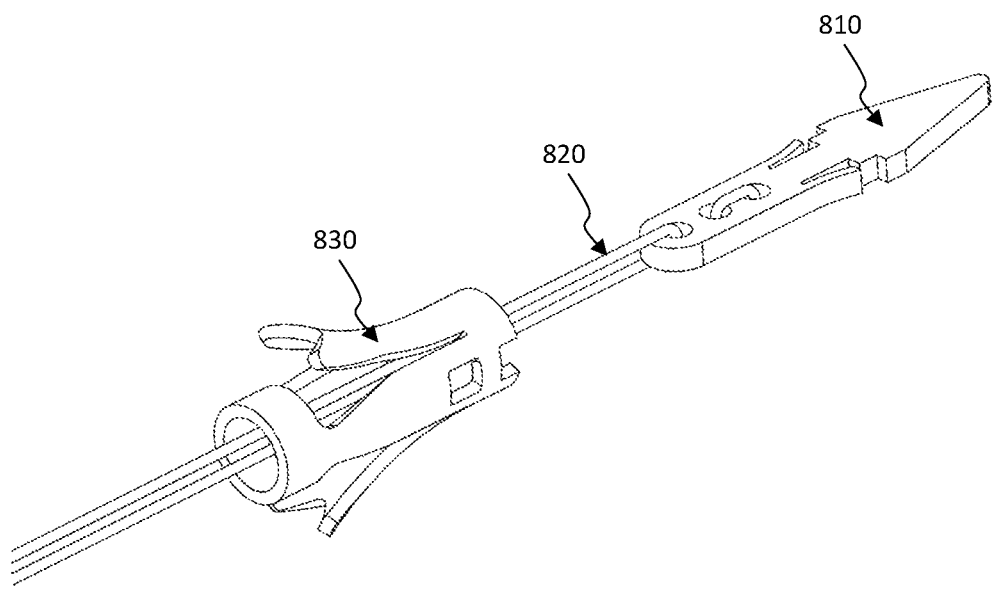
FIGS. 14A, 14B and 14C are simplified respective pictorial view, side view and sectional illustrations of a further stage in the assembly of the anchor assembly of FIGS. 8A-12D, FIG. 14C being taken along lines C-C in FIG. 14B.
Figure 14B:
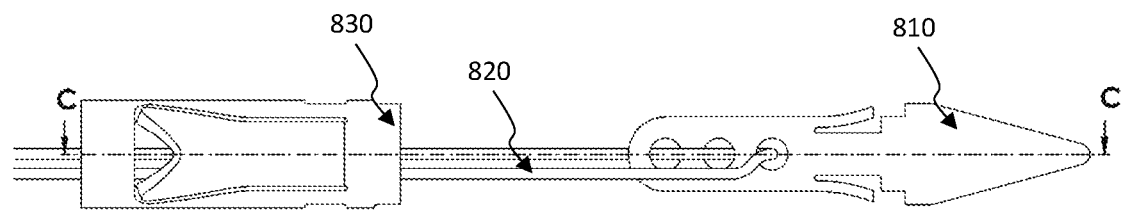
Figure 14C:
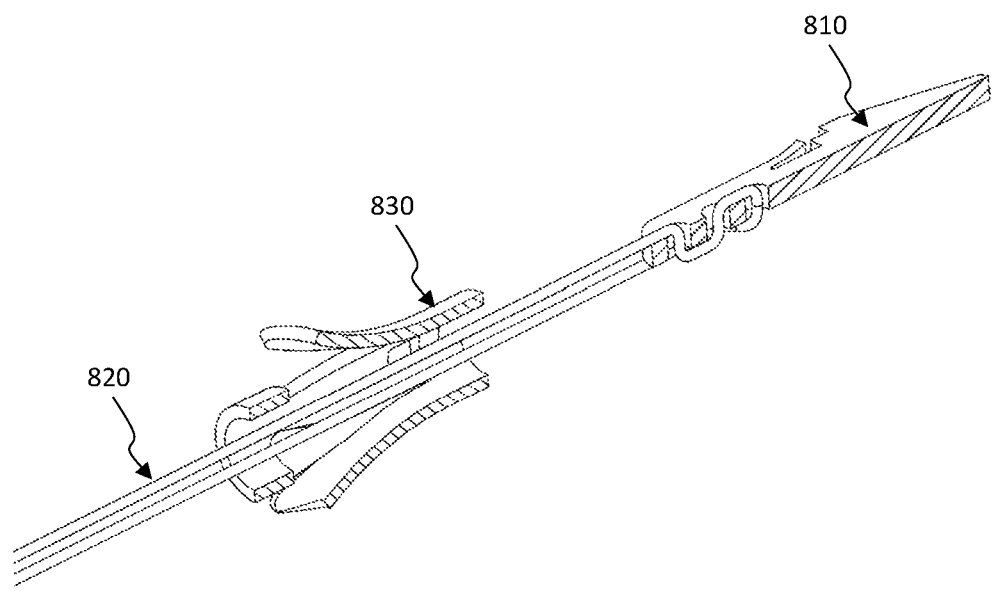
Figure 15A:
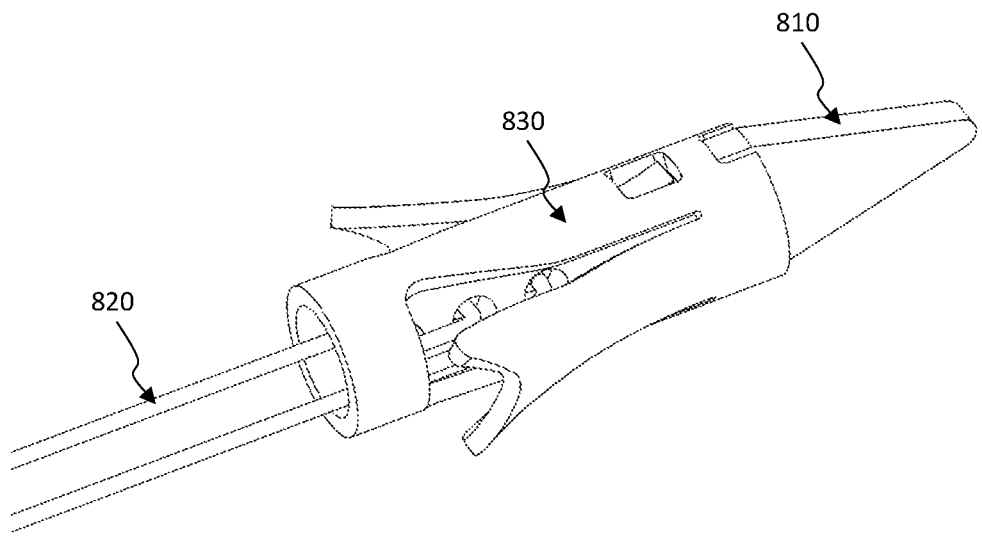
FIGS. 15A, 15B and 15C are simplified respective pictorial view, side view and sectional illustrations of a still further stage in the assembly of the anchor assembly of FIGS. 8A-12D, FIG. 15C being taken along lines C-C in FIG. 15B.
Figure 15B:
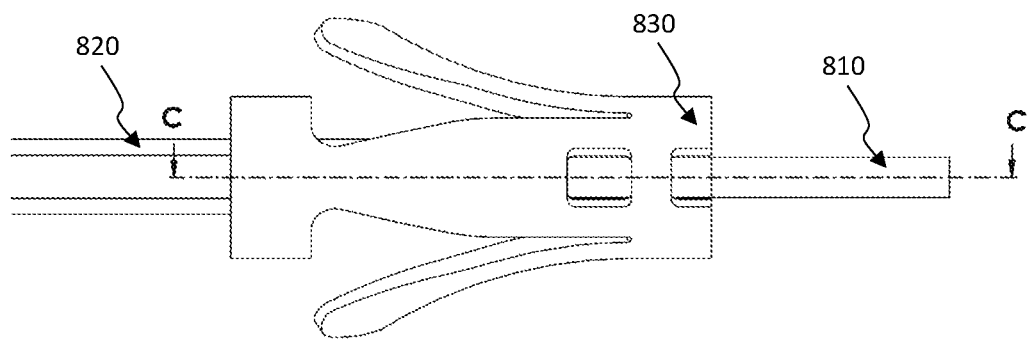
Figure 15C:
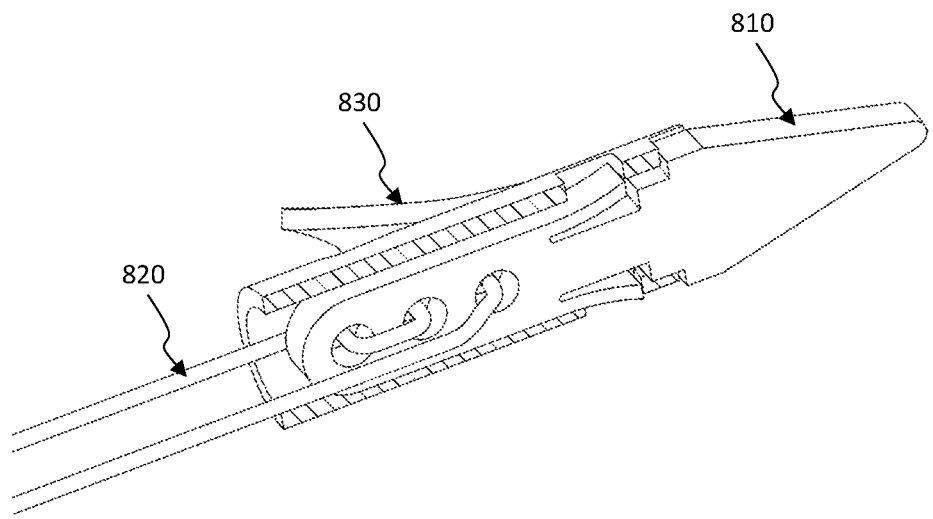

Reference is now made to FIGS. 13A-15C, which illustrate the assembly of the anchor assembly of FIGS. 8A-12D. FIGS. 13A, 13B & 13C show threading of the flexible elongate element 820 through apertures 850 in the penetrating element 810. FIGS. 14A, 14B and 14C show the anchoring element 830 sliding over the two filaments of the flexible elongate element 820. FIGS. 15A, 15B and 15C show the anchoring element 830 fully engaged and locked to the penetrating element 810.

Figure 16A:
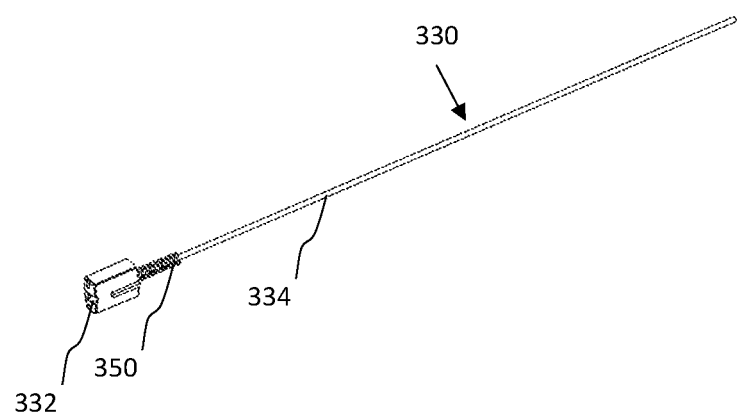
FIGS. 16A, 16B, 16C, 16D, 16E and 16F are simplified illustrations of stages in the assembly of the anchor insertion assembly of FIGS. 3A-7C.
Figure 16B:
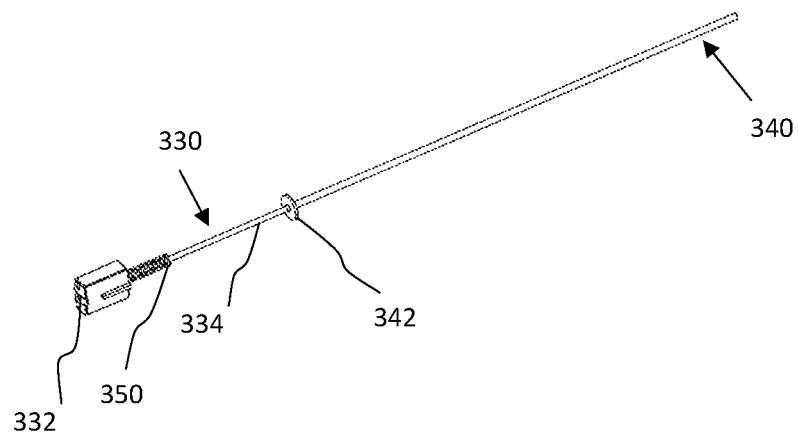
Figure 16C:
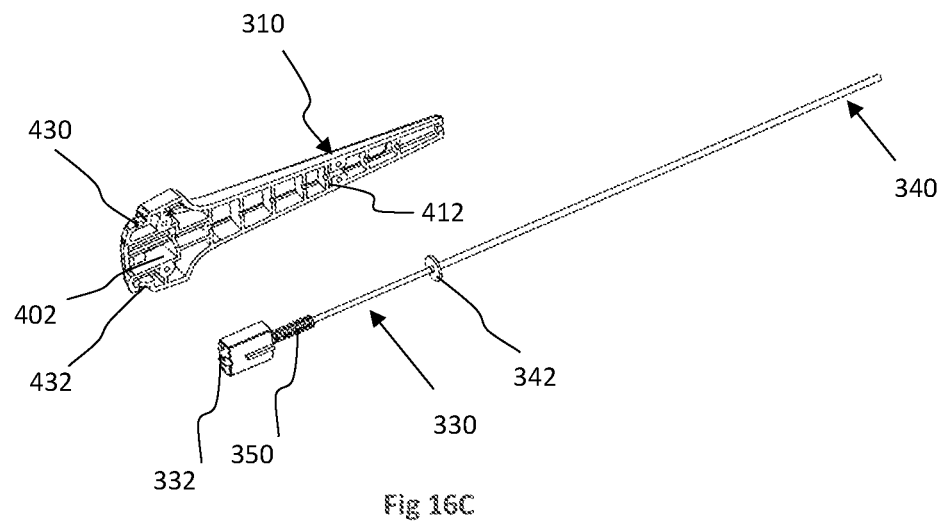
Figure 16D:
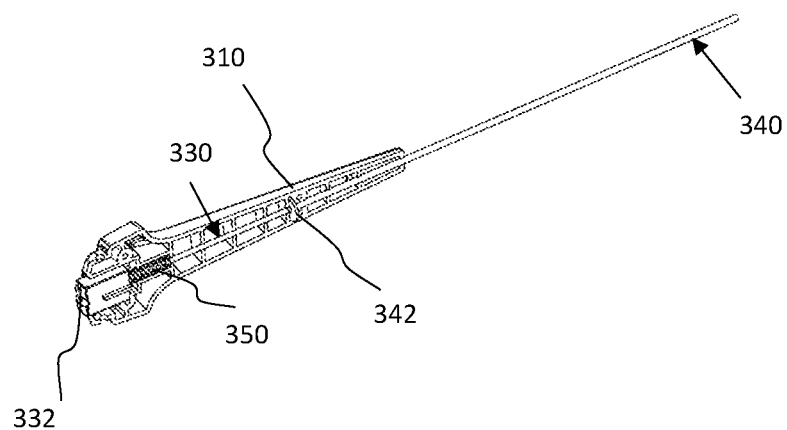

Reference is now made to FIGS. 16A, 16B, 16C, 16D, 16E and 16F, which are simplified illustrations of stages in the assembly of the anchor insertion assembly of FIGS. 3A-7C. As seen in FIG. 16A, coil spring 350 is mounted over elongate tube 334 of inner tube and button assembly 330 adjacent button 332. As seen in FIG. 16B, the assembly of FIG. 16A is inserted into outer tube and retainer assembly 340. As seen in FIGS. 16C and 16D, the assembly of FIG. 16B is inserted into engagement with first housing portion 310. Specifically button 332 is inserted into socket 402 and button retaining disk 342 is inserted into socket 412.

Figure 16E:
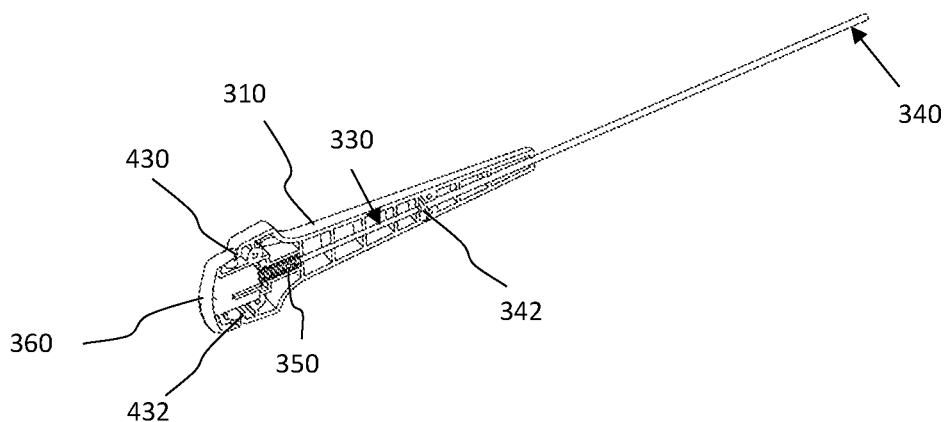
Figure 16F:
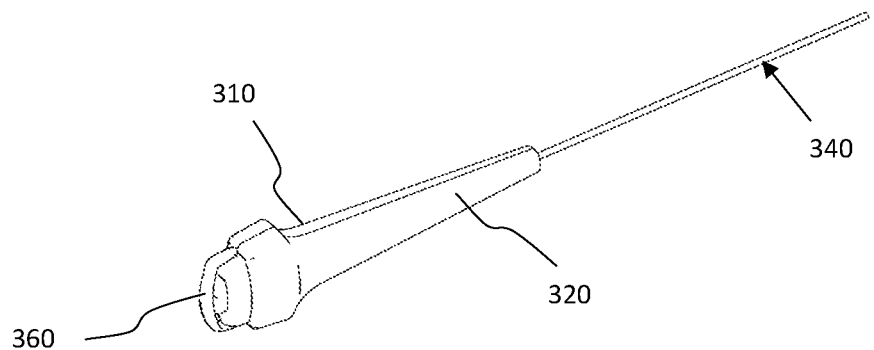

FIG. 16E illustrates pivotal mounting of button guard element 360 onto pivot mount sockets 430 and 432 of first housing portion 310 for selectable protective engagement with button 332. FIG. 16F shows joining of the first and second housing portions 310 and 320 as a final assembly step.

Figure 17A:
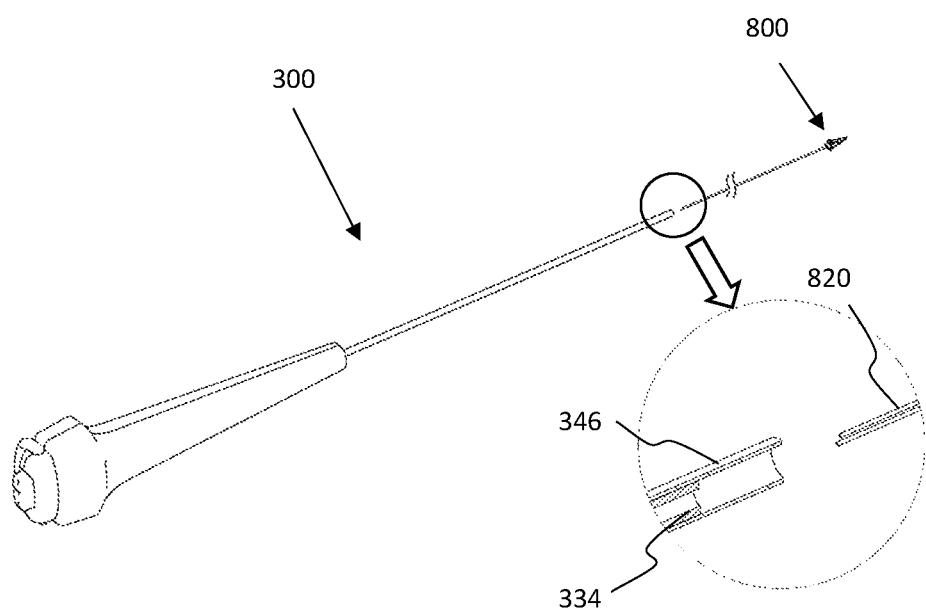
FIGS. 17A, 17B, 17C, 17D, 17E and 17F are simplified illustrations of stages in the insertion of the anchor assembly of FIGS. 8A-12D into the anchor insertion assembly of FIGS. 3A-7C.
Figure 17B:
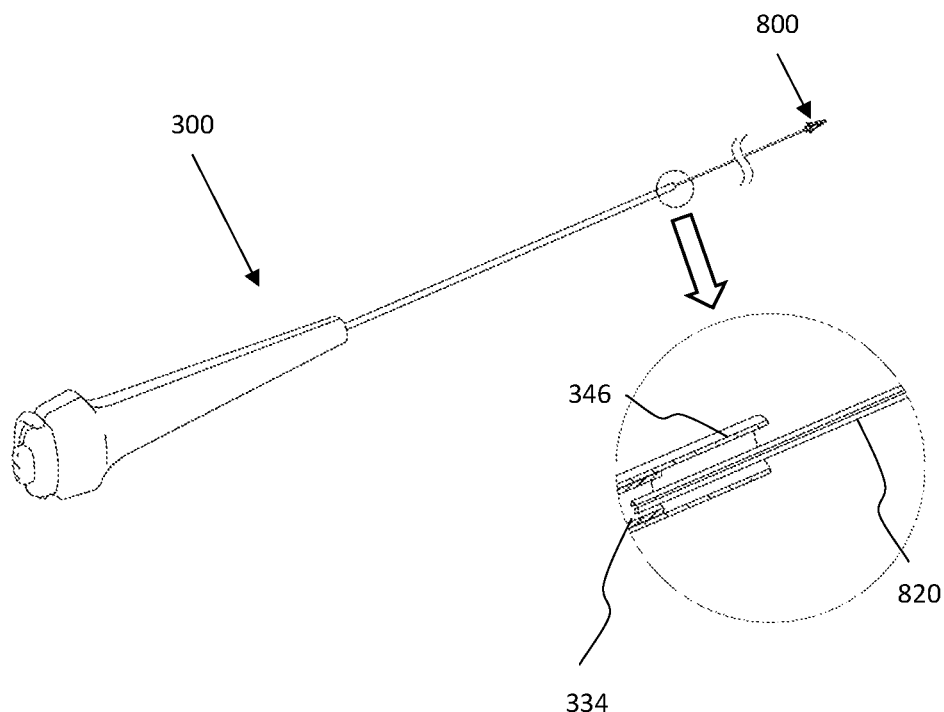
Figure 17C:
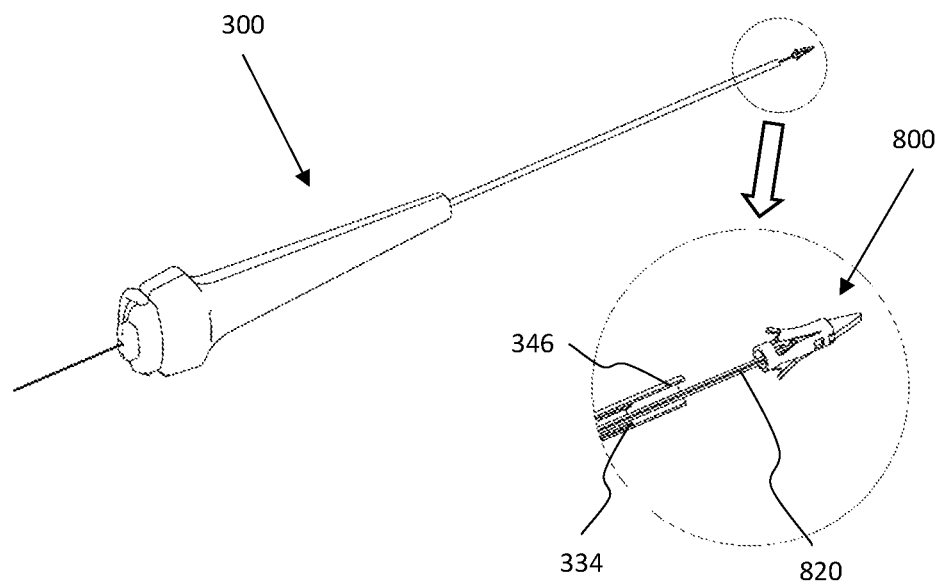

Reference is now made to FIGS. 17A, 17B, 17C, 17D, 17E and 17F, which are simplified illustrations of stages in the insertion of the anchor assembly 800 of FIGS. 8A-12D into the anchor insertion assembly 300 of FIGS. 3A-7C. As seen in FIG. 17A, the anchor assembly 800 is arranged forwardly of the anchor insertion assembly 300, ready for insertion. FIG. 17B shows initial threading of the two filaments of flexible elongate element 820 of the anchor assembly 800 into generally coaxial elongate tubes 334 and 346 of the anchor insertion assembly 300. FIG. 17C shows the anchor assembly 800 nearly fully inserted into the anchor insertion assembly 300.

Figure 17D:
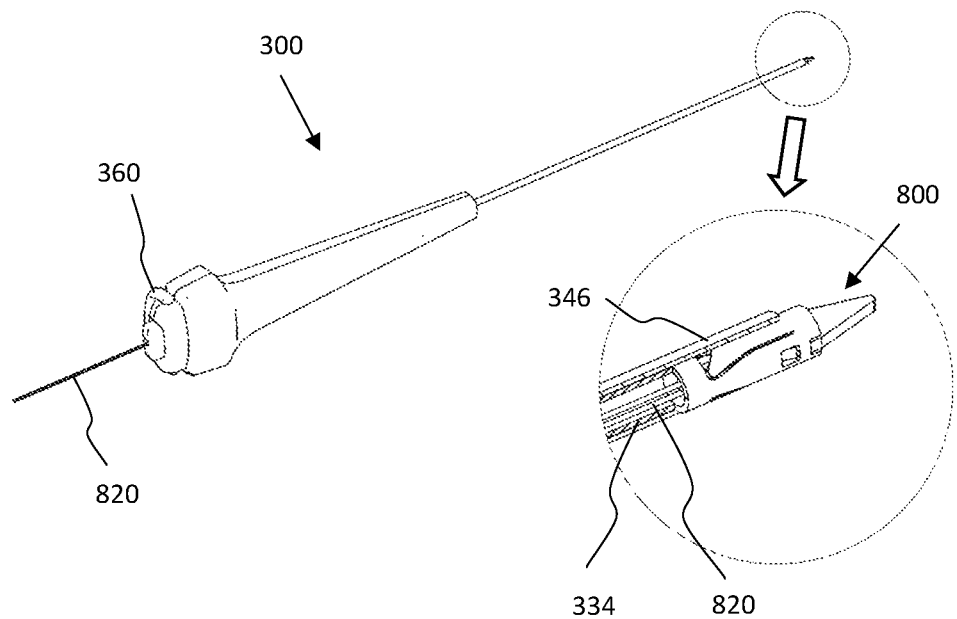

Thereafter, the anchoring element 830 is manually or otherwise squeezed into its compressed state. FIG. 17D shows the anchor assembly 800 fully inserted into the anchor insertion assembly 300, such that the anchoring element 830 is retained in its compressed state by virtue of its engagement with an inner surface of elongate tube 346. It is also seen that the free ends of the two filaments of flexible elongate element 820 of the anchor assembly 800 extend straight out through aperture 512 in surface 504 at transverse slit 508 of button 332.

Figure 17E:
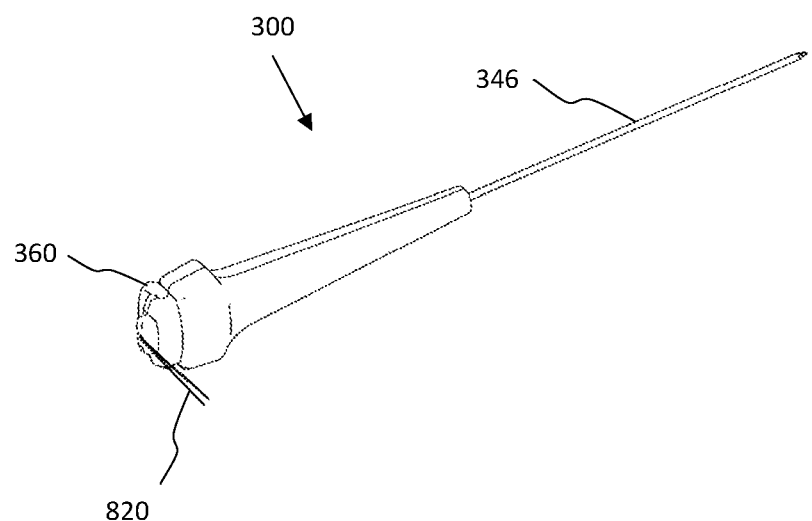
Figure 17F:
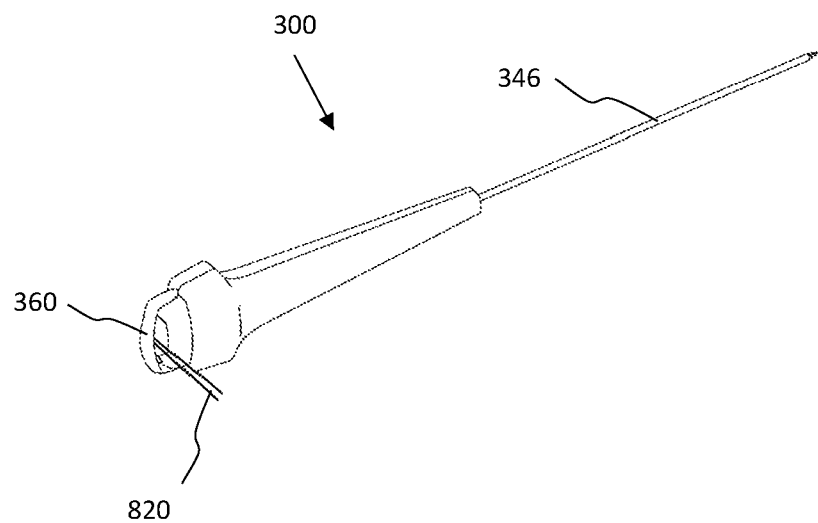

Reference is now made to FIG. 17E, which shows bending of the two filaments of flexible elongate element 820 of the anchor assembly 800 to extend along transverse slit 508 of button 332. FIG. 17F illustrates a final assembly step wherein button guard element 360 is pivotably rotated relative to first and second housing portions 310 and 320 and over the two filaments of flexible elongate element 820 into selectable protective engagement with button 332.

Reference is now made to FIGS. 18A, 18B, 18C, 18D, 18E, 18F, 18G, 18H, 18I and 18J, which are simplified illustrations of stages in the operation of the anchoring device of FIGS. 1A-17F for use with a left index finger.

Figure 18A:
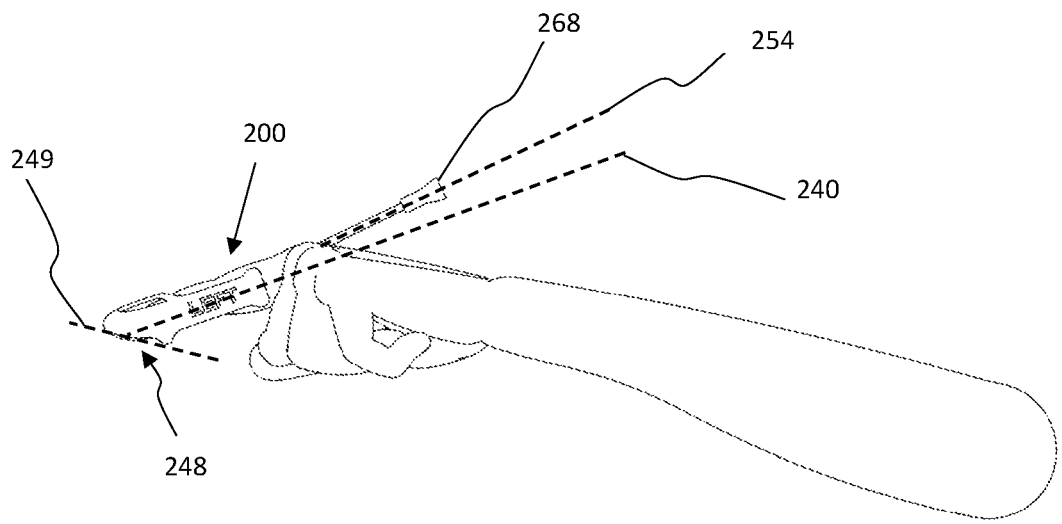
FIGS. 18A, 18B, 18C, 18D, 18E, 18F, 18G, 18H, 18I and 18J are simplified illustrations of stages in the operation of the anchoring device of FIGS. 1A-17F.

As seen in FIG. 18A, the left index finger of a user is inserted into the finger-mountable work channel defining assembly 200 and extends generally along finger mounting axis 240 thereof. As noted above, finger mounting axis 240 lies in a finger mounting axis plane 253 and work channel axis 254 lies in a work channel axis plane 255, which is parallel to the finger mounting axis plane 253. The distal phalanx of the left index finger of the user extends through opening 248 which lies in aperture plane 249 and is orthogonal to the mutually parallel finger mounting axis plane 253 and to the work channel axis plane 255.

Figure 18B:
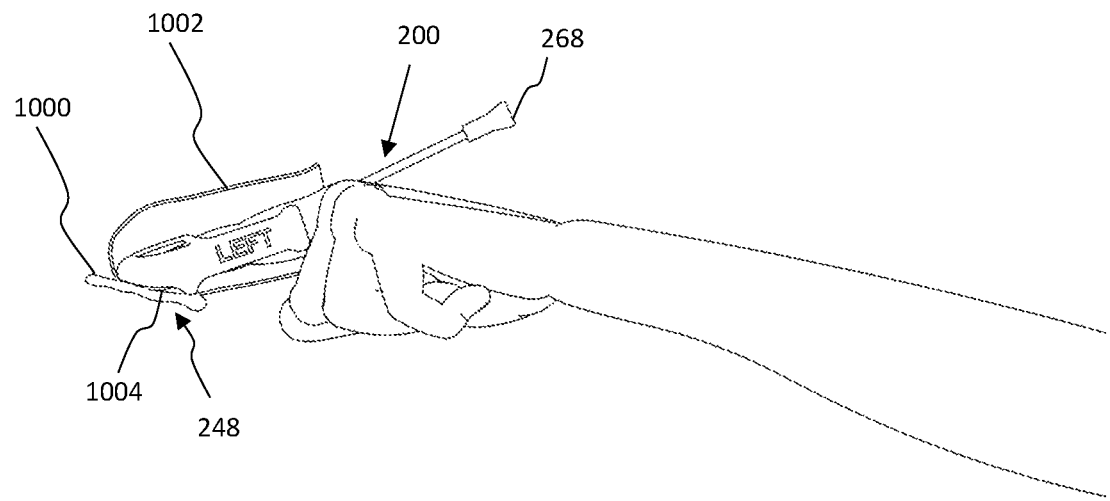

FIG. 18B shows the distal phalanx of the left index finger of the user in engagement with a portion of an anchoring substrate designated by reference numeral 1000. It is appreciated that index finger may be in direct or indirect engagement with anchoring substrate 1000. The anchoring substrate 1000 may be any suitable anchoring substrate. One example is a sacrospinous ligament, which lies behind a vaginal wall, here designated by reference numeral 1002, which is in contact with the distal phalanx of the left index finger, here designated by reference numeral 1004.

Figure 18C:
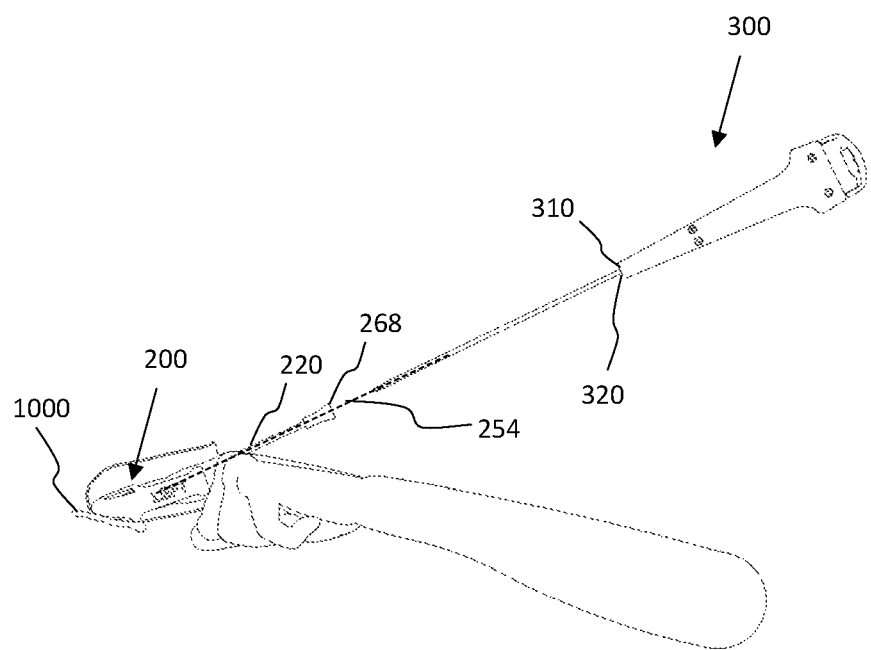

FIG. 18C shows the anchor insertion assembly 300 axially aligned with the work channel axis 254 and about to be inserted in the work channel defining element 220 of the finger-mountable work channel defining assembly 200. The anchor insertion assembly 300 is preferably in its operative orientation shown in FIG. 17F, wherein the anchor assembly 800 is preloaded therein, as described hereinabove with reference to FIGS. 17A-17F.

Figure 18D:
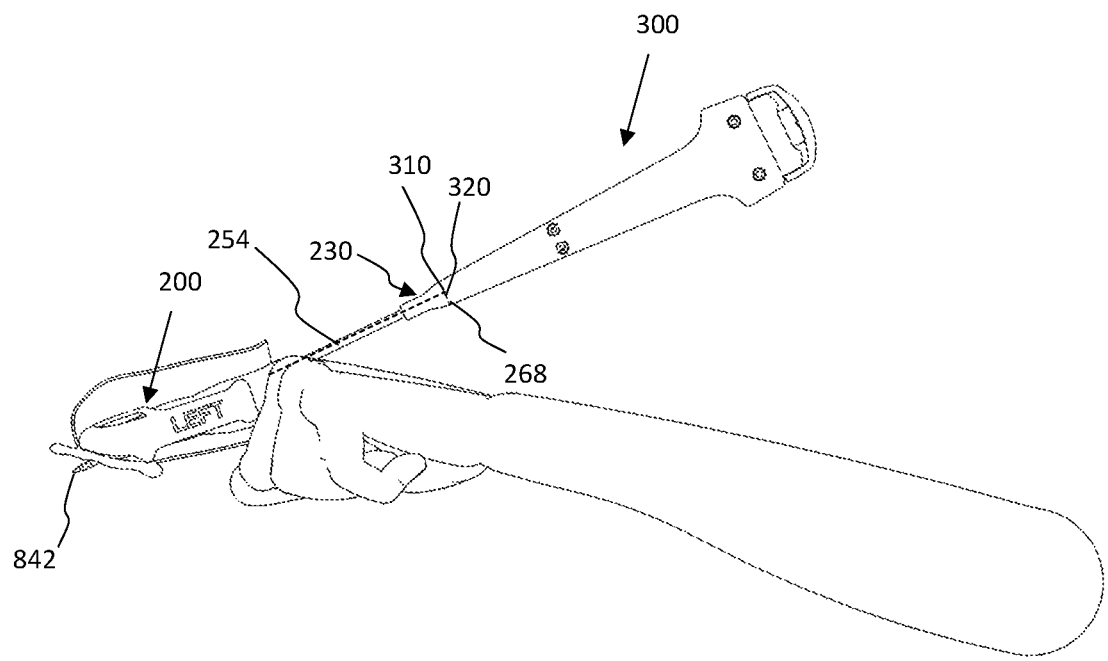
Figure 18E:
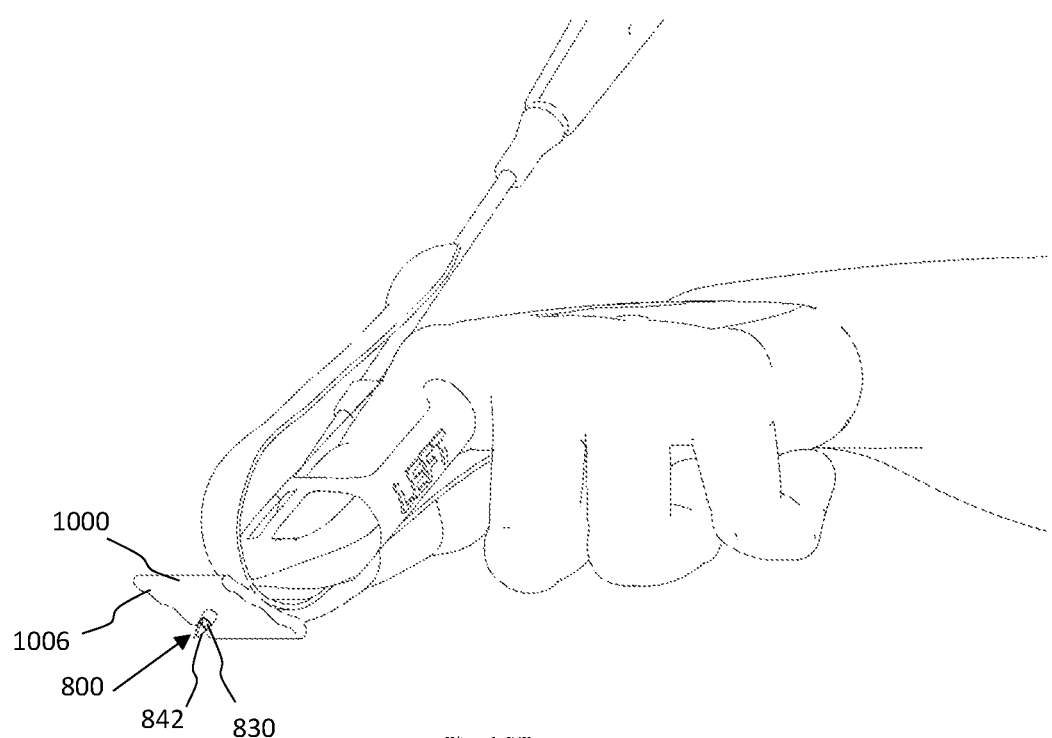

FIGS. 18D and 18E show the anchor insertion assembly 300 fully inserted into the work channel defining element 220 of the finger-mountable work channel defining assembly 200 along work channel axis 254. It is a particular feature of an embodiment of the present invention that the extent of insertion of the anchor insertion assembly in work channel defining element 220, and thus the extent to which the penetrating element 810 extends beyond the aperture plane 249 at this stage, is limited by engagement of forward end surface 448 of the first and second housing portions 310 and 320 with edge 268 of insertion and stop defining element 230. Preferably, the extent that the tip of edge 842 of penetrating element 810 extends along the work channel axis 254 beyond the aperture plane 249 is between 10-20 mm and more preferably 14-17 mm and most preferably 15.5 mm.

FIGS. 18D and 18E also show the forwardmost portions of the anchor insertion assembly 300 and of the anchor assembly 800 having penetrated the anchoring substrate 1000 and having been inserted therein. The anchoring element 830 is retained in its compressed state inasmuch as it is located partially within elongate tube 346 of inner tube and button assembly 330.

Figure 18F:
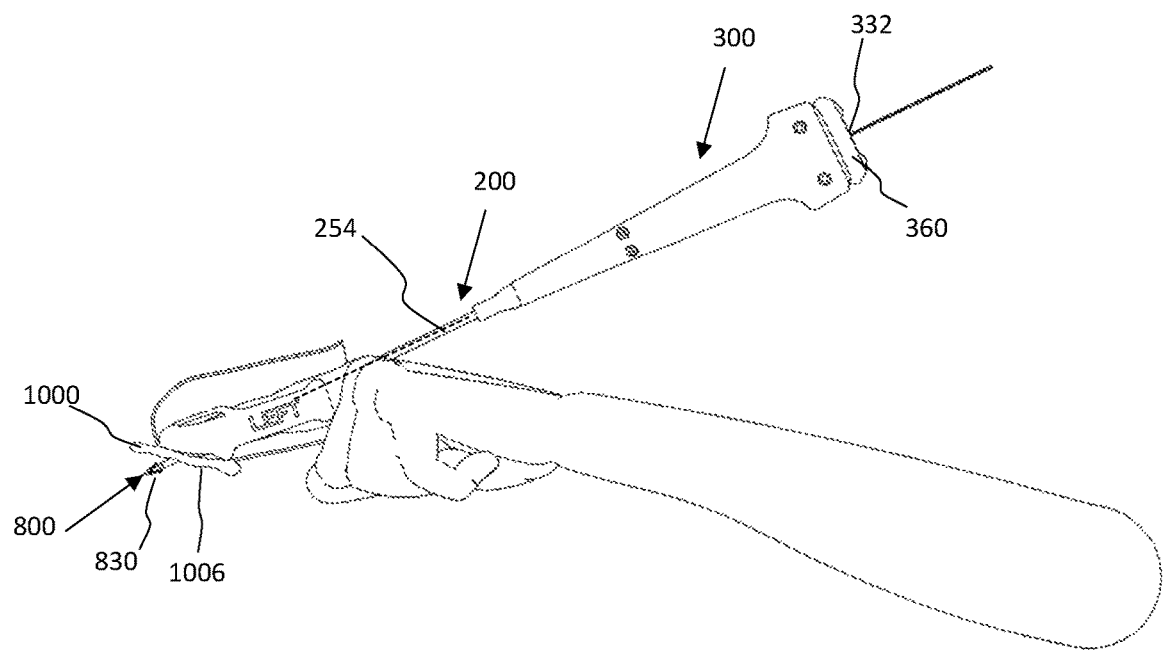
Figure 18G:
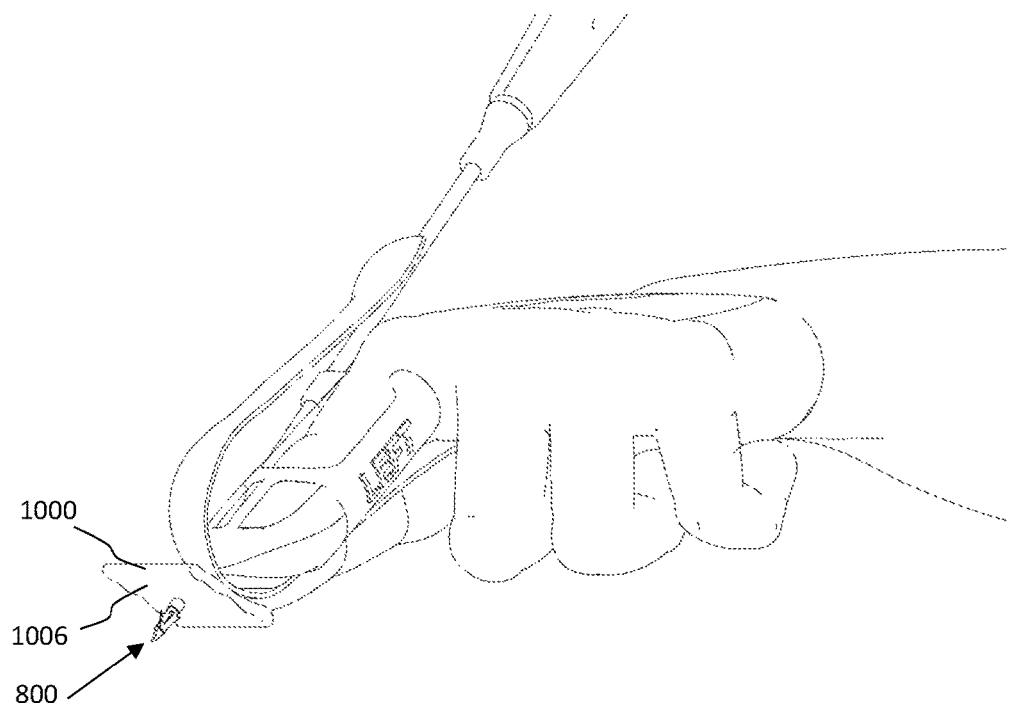

FIGS. 18F and 18G show pressing of button 332 following rotation of the button guard element 360 to its orientation shown in FIG. 17E. Pressing of button 332 preferably causes the anchor assembly 800 to be further displaced by coil spring 350 along the work channel axis 254, preferably by a distance therealong of 5 mm. This displacement causes the anchoring element 830 to be located fully forward of elongate tube 346 and thus forward of the anchoring substrate 1000 and to assume its non-compressed state, as seen in FIG. 8A. In this operative orientation, rearwardly facing edge surfaces 906 of flaps 904, which define flap feet 908, lie forward of the anchoring substrate 1000 and are spaced from a surface 1006 thereof.

Figure 18H:
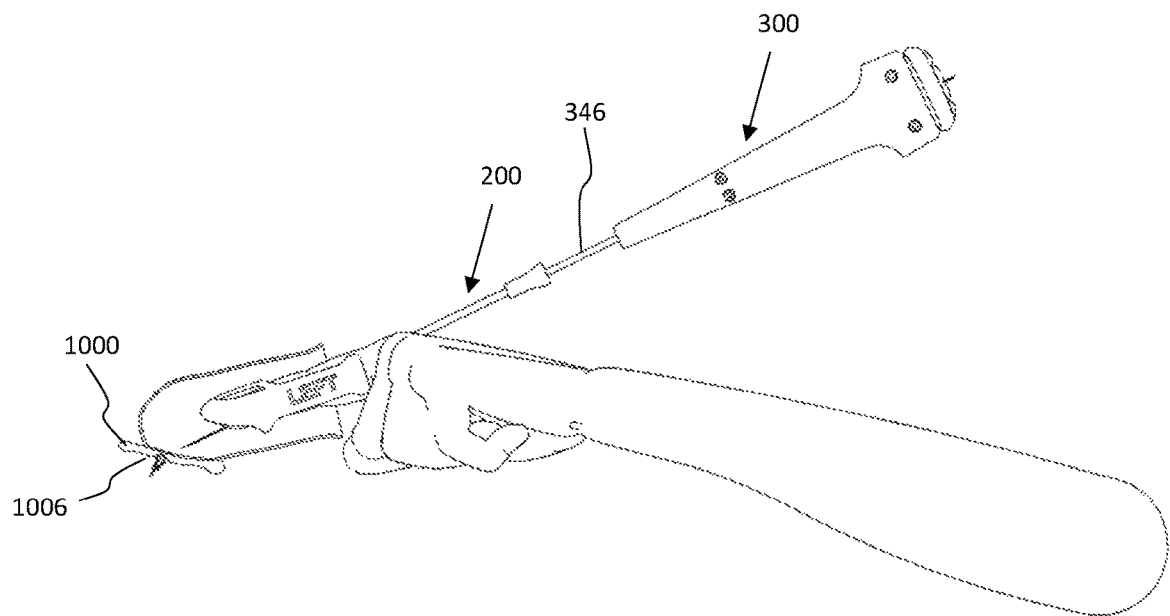
Figure 18I:
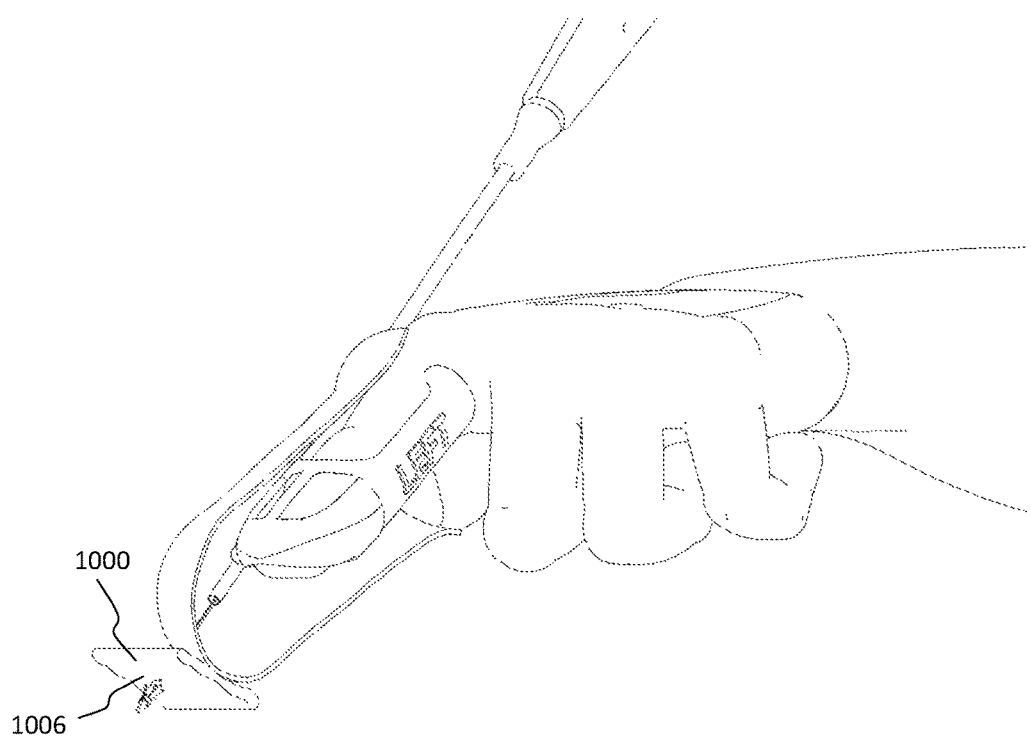

FIGS. 18H and 18I show retraction of the anchor insertion assembly 300 along work channel axis 254 such that rearwardly facing edge surfaces 906 of flaps 904 engage surface 1006 of anchoring substrate 1000 and do not permit the anchoring assembly to be disengaged therefrom, thus producing anchoring of the flexible elongate element 820 onto anchoring substrate 1000.

Figure 18J:
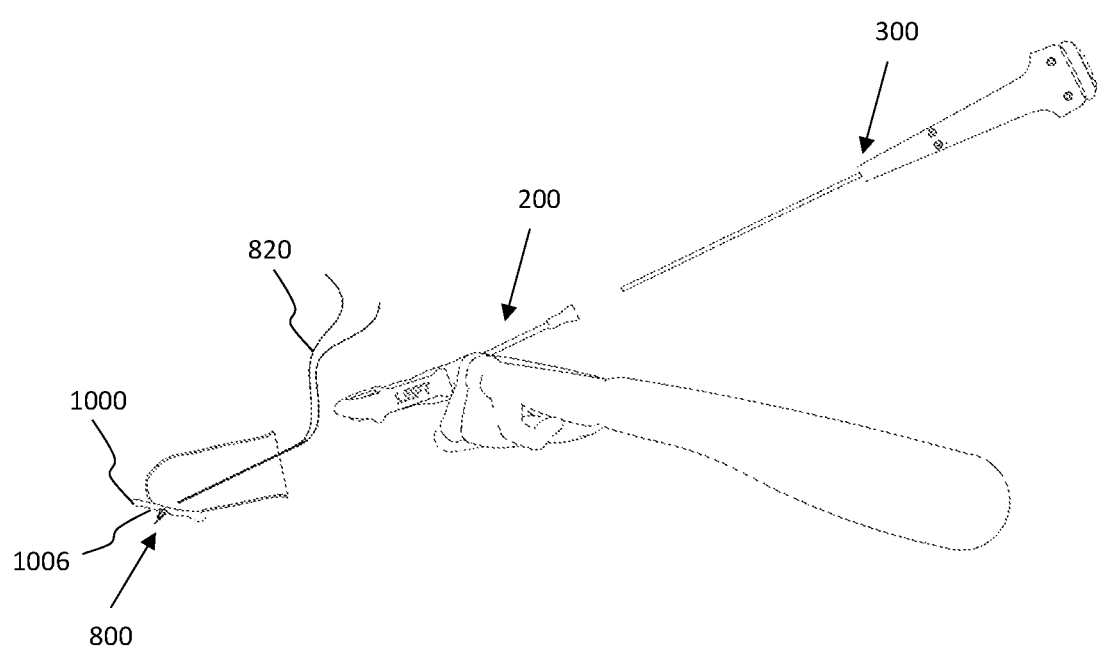

FIG. 18J shows disengagement of the finger-mountable work channel defining assembly 200 and the anchor insertion assembly 300 from the anchor assembly 800, leaving the flexible elongate element 820 anchored onto the anchoring substrate 1000 by means of the anchoring element 830.

It will be appreciated by persons skilled in the art that the present invention is not limited to what has been particularly shown and described hereinabove. Rather the scope of the present invention includes both combinations and subcombinations of various features described hereinabove and modifications thereof, which are not in the prior art.

The invention claimed is:

1. An anchoring device comprising:
    a finger-mountable work channel defining assembly defining two side walls joined at an end wall, said finger mountable work channel defining assembly defining a finger mounting axis, said finger mountable work channel defining assembly defining a work channel axis along one of said side walls, said finger-mountable work channel defining assembly defining an aperture lying generally in an aperture plane angled with respect to said finger mounting axis and with respect to said work channel axis;
    an anchor insertion assembly arranged for axial displacement along said work channel axis with respect to said aperture so as to intersect said aperture plane; and
    an anchor assembly including at least an anchoring portion and a flexible elongate portion attached thereto, said anchoring portion having a pre-anchoring operative orientation and an anchoring operative orientation, said anchoring portion of said anchor assembly including a penetrating element and an anchoring element;
    said penetrating element including a pointed forward portion, a neck portion and a rearward engagement portion, said rearward engagement portion including a pair of flexible retaining fingers integrally formed therewith; and
    said anchoring element including a pair of retaining apertures, said pair of retaining apertures arranged for insertion of said flexible retaining fingers thereinto, and for retaining said pair of flexible retaining fingers of said penetrating element therein.

2. The anchoring device according to claim 1, wherein said anchor insertion assembly is arranged for limited axial displacement along said work channel axis with respect to said aperture so as to intersect said aperture plane.

3. The anchoring device according to claim 1, wherein said anchor insertion assembly is arranged for axial displacement along said work channel axis with respect to said aperture so as to intersect said aperture plane adjacent said aperture.

4. The anchoring device according to claim 1, wherein said anchoring portion is displaceable along said work channel axis across said aperture plane by said anchor insertion assembly while in said pre-anchoring operative orientation.

5. The anchoring device according to claim 1, wherein said finger mounting axis lies in a finger mounting axis plane, said work channel axis lies in a work channel axis plane, which is parallel to said finger mounting axis plane and said aperture plane is orthogonal to said mutually parallel finger mounting axis plane and to said work channel axis plane.

6. The anchoring device according to claim 1, wherein said work channel axis angled with respect to said finger mounting axis.

7. The anchoring device according to claim 1, wherein said finger-mountable work channel defining assembly defines a finger anchoring location engagement portion lying generally in an orientation angled with respect to said work channel axis.

8. The anchoring device according to claim 1, wherein said finger mountable work channel defining assembly is configured to be right or left hand specific.

9. The anchoring device according to claim 1, wherein said finger mountable work channel defining assembly comprises a finger mount element, an elongate work channel defining element and an insertion and stop defining element, which is fixedly mounted onto said elongate work channel defining element.

10. The anchoring device according to claim 9, wherein said finger mountable work channel defining assembly is formed as a single piece of a partially flexible plastic material and is configured to enable an underside of the operator's finger to engage an anchoring site.

11. The anchoring device according to claim 9, wherein said work channel defining assembly defines forward and rearward throughgoing fixed mounting channels for fixedly mounting of said elongate work channel defining element.

12. The anchoring device according to claim 9, wherein said insertion and stop defining element is a hollow element includes a generally cylindrical hollow portion which communicates with a hollow funnel-shaped portion defining an edge, which serves as a precise stop limiting the axial extent of displacement of the anchor insertion assembly therethrough.

13. The anchoring device according to claim 1, wherein said anchor insertion assembly comprises first and second housing portions onto which are mounted an inner tube and button assembly including a button and an elongate tube fixedly mounted thereto at an end of said elongate tube.

14. The anchoring device according to claim 13, further comprising an outer tube and retainer assembly mounted onto said first and second housing portions.

15. The anchoring device according to claim 14, wherein said outer tube and retainer assembly includes a retaining disk, which is fixedly mounted onto an end of an elongate tube and a coil spring mounted over said elongate tube between said button and said retaining disk.

16. The anchoring device according to claim 15, further comprising a button guard element pivotably mounted onto said first and second housing portions for selectable protective engagement with said button.

17. The anchoring device according to claim 13, wherein said button is configured to have an engagement surface formed with a pair of retaining recesses arranged on opposite sides of a transverse slit and an axial bore, which extends therethrough and defines an aperture in said engagement surface at said transverse slit.

18. A method for utilizing an anchoring device for positioning and inserting an anchoring assembly into an anchoring substrate, the anchoring device comprising:
 a finger-mountable work channel defining assembly defining two side walls joined at an end wall, said finger mountable work channel defining assembly defining a finger mounting axis, said finger mountable work channel defining assembly defining a work channel axis along one of said side walls, said finger-mountable work channel defining assembly defining an aperture lying generally in an aperture plane angled with respect to said finger mounting axis and with respect to said work channel axis;
 an anchor insertion assembly arranged for axial displacement along said work channel axis with respect to said aperture so as to intersect said aperture plane; and
 an anchor assembly including at least an anchoring portion and a flexible elongate portion attached thereto, said anchoring portion having a pre-anchoring operative orientation and an anchoring operative orientation, said anchoring portion of said anchor assembly including a penetrating element and an anchoring element;
 said penetrating element including a pointed forward portion, a neck portion and a rearward engagement portion, said rearward engagement portion including a pair of flexible retaining fingers integrally formed therewith; and
 said anchoring element includes a pair of retaining apertures, said pair of retaining apertures arranged for insertion of said flexible retaining fingers thereinto, and for retaining said pair of flexible retaining fingers of said penetrating element therein;
 the method comprising:
 inserting a finger of a user into said finger-mountable work channel defining assembly, whereby a distal phalanx of said finger is arranged so as to engage said anchoring substrate; and
 inserting said anchor insertion assembly into said finger-mountable work assembly with said anchor assembly preloaded therein, along said work channel axis, such that the orientation of said finger of said user precisely defines the location of anchoring engagement of said anchor assembly with said anchoring substrate.

19. The method according to claim 18, wherein an extent of insertion of said anchor assembly in said anchoring substrate is precisely limited by engagement between said anchor insertion assembly and said finger-mountable work channel defining assembly.

20. The anchoring device according to claim 15, wherein each of said first and second housing portions include multiple structural internal ribs, said ribs defining:
 a first pair of sockets for accommodating said button and permitting limited axial translation thereof along an axis; and
 a second pair of sockets for accommodating said retaining disk and preventing axial translation thereof along said axis.

* * * * *